United States Patent
Steendam et al.

(10) Patent No.: US 10,300,019 B2
(45) Date of Patent: May 28, 2019

(54) BIODEGRADABLE, SEMI-CRYSTALLINE, PHASE SEPARATED, THERMOPLASTIC MULTI BLOCK COPOLYMERS FOR CONTROLLED RELEASE OF BIOLOGICALLY ACTIVE COMPOUNDS

(71) Applicant: InnoCore Technologies B.V., Groningen (NL)

(72) Inventors: Rob Steendam, Groningen (NL); Theodorus Adrianus Cornelius Flipsen, Groningen (NL); Christine Hiemstra, Groningen (NL); Johan Zuidema, Groningen (NL)

(73) Assignee: InnoCore Technologies B.V., Groningen (NL)

( * ) Notice: Subject to any disclaimer, the term of this patent is extended or adjusted under 35 U.S.C. 154(b) by 1 day.

(21) Appl. No.: 15/677,442

(22) Filed: Aug. 15, 2017

(65) Prior Publication Data
US 2018/0085318 A1 Mar. 29, 2018

Related U.S. Application Data

(63) Continuation of application No. 14/233,961, filed as application No. PCT/NL2012/050529 on Jul. 23, 2012, now abandoned.

(30) Foreign Application Priority Data

Jul. 22, 2011 (EP) ..................................... 11174987

(51) Int. Cl.
*A61K 9/48* (2006.01)
*A61K 9/70* (2006.01)
(Continued)

(52) U.S. Cl.
CPC .............. *A61K 9/4816* (2013.01); *A61K 9/08* (2013.01); *A61K 9/1629* (2013.01);
(Continued)

(58) Field of Classification Search
CPC .. A61K 9/4816; A61K 9/7007; A61K 9/5031; A61K 9/5021; A61K 9/1629;
(Continued)

(56) References Cited

U.S. PATENT DOCUMENTS 4,429,080 A 1/1984 Casey et al.
5,066,772 A 11/1991 Tang et al.
(Continued)

FOREIGN PATENT DOCUMENTS

EP 1382628 * 1/2004 ............. C08G 63/08
EP 1382628 A1 1/2004
(Continued)

OTHER PUBLICATIONS

Kissel et al, "Parenteral protein delivery systems using biodegradable polyesters of ABA block structure, containing hydrophobic poly(lactide-co-glycolide) A blocks and hydrophilic poly(ethyleneoxide) B blocks", Journal of Controlled Release, vol. 39, pp. 315-326, 1996.
(Continued)

*Primary Examiner* — Trevor Love
(74) *Attorney, Agent, or Firm* — Hoffmann & Baron, LLP

(57) ABSTRACT

This invention is directed to a biodegradable, semi-crystalline, phase separated thermoplastic multi-block copolymer, a process for preparing said multi-block copolymer, a composition for the delivery of at least one biological active compound, and to a method for delivering a biologically active compound to a subject in need thereof.

A multi-block copolymer of the invention is characterized in that:

(Continued)

a) it comprises at least one hydrolysable pre-polymer (A) segment and at least one hydrolysable pre-polymer (B) segment,
b) said multi-block copolymer having a $T_g$ of 37° C. or less and a $T_m$ of 110-250° C. under physiological conditions;
c) the segments are linked by a multifunctional chain-extender;
d) the segments are randomly distributed over the polymer chain;
e) at least part of the pre-polymer (A) segment is derived from a water-soluble polymer.

34 Claims, 11 Drawing Sheets

(51) Int. Cl.
  *A61K 9/50* (2006.01)
  *A61K 9/16* (2006.01)
  *A61K 9/08* (2006.01)
  *C08L 87/00* (2006.01)
  *C08G 81/00* (2006.01)
(52) U.S. Cl.
  CPC .......... *A61K 9/1641* (2013.01); *A61K 9/5021* (2013.01); *A61K 9/5031* (2013.01); *A61K 9/7007* (2013.01); *C08G 81/00* (2013.01); *C08L 87/005* (2013.01)
(58) Field of Classification Search
  CPC ....... A61K 9/1641; A61K 9/08; C08L 87/005; C08G 81/00
  See application file for complete search history.

(56) References Cited

U.S. PATENT DOCUMENTS

| 5,133,739 | A | 7/1992 | Beswada et al. |
| 5,236,444 | A | 8/1993 | Muth et al. |
| 5,554,170 | A | 9/1996 | Roby et al. |
| 5,711,958 | A | 1/1998 | Cohn et al. |
| 5,980,948 | A | 11/1999 | Goedemoed et al. |
| 6,160,084 | A | 12/2000 | Langer et al. |
| 2006/0140999 | A1 | 6/2006 | Lendlein et al. |

FOREIGN PATENT DOCUMENTS

| EP | 1555278 | 7/2005 |
| WO | 9902168 | 1/1999 |
| WO | 2004007588 | 1/2004 |

OTHER PUBLICATIONS

Jong et al, "Monodisperse Enantiomeric Lactic Acid Oligomers: Preparation, Characterization, and Stereocomplex Formation", Macromolecules, vol. 31, No. 19, Sep. 22, 1998.
Penco et al, "Multiblock Copolymers Based on Segments of Poly (D,L-lactic-glycolic acid) and Poly(ethylene glycol) or Poly(•-caprolactone): A Comparison of Their Thermal Properties and Degradation Behavior", Journal of Applied Polymer Science, vol. 78, pp. 1721-1738, 2000.
Meinel et al, "Stabilizing insulin-like growth factor-I in poly(D,L-lactide-co-glycolide) microspheres", Journal of Controlled Release, vol. 70, pp. 193-202, 2001.
Lee et al, "Thermoreversible gelation of biodegradable poly(•-caprolactone) and poly(ethylene glycol) multiblock copolymers in aqueous solutions", Journal of Controlled Release, vol. 73, pp. 315-327, 2001.
Crommelin et al, "Shifting paradigms: biopharmaceuticals versus low molecular weight drugs", International Journal of Pharmaceutics, vol. 266, pp. 3-16, 2003.
Okada, "One- and three-month release injectable microspheres of the LH-RH superagonist leuprorelin acetate"; Advanced Drug Delivery Reviews, vol. 28, pp. 43-70, 1997.
Verkerke, et al, "Determining the centre of pressure during walking and running using an instrumented treadmill," Journal of Biomechanics, vol. 38, pp. 1881-1885, 2005.
Lin, et al, "Effect of plantar desensitization on postural adjustments prior to step initiation," Gait & Posture, vol. 34, pp. 451-456, 2011.

* cited by examiner

| Band | Sample | Band | Sample |
|---|---|---|---|
| 1 | IGF-1 fresh | 6 | UT medium 1 wk |
| 2 | Marker | 7 | UT medium 2 wk |
| 3 | UT 1 wk | 8 | Marker |
| 4 | UT low 1 wk | 9 | UT high, 1 wk |
| 5 | UT low 2 wk | 10 | IFG-1 fresh |

BIODEGRADABLE, SEMI-CRYSTALLINE, PHASE SEPARATED, THERMOPLASTIC MULTI BLOCK COPOLYMERS FOR CONTROLLED RELEASE OF BIOLOGICALLY ACTIVE COMPOUNDS

The present application is a continuation of, claims priority to, and incorporates by reference in its entirety U.S. Ser. No. 14/233,961 filed Mar. 6, 2014, which in turn is a national stage entry of PCT/NL2012/050529, filed Jul. 23, 2012, which claims priority to European patent application number 11174987, filed Jul. 22, 2011.

The invention is directed to biodegradable, semi-crystalline, phase separated, thermoplastic multi-block copolymers, a process for preparing said multi-block copolymers, composition for the delivery of at least one biologically active compound, and to methods for delivering a biologically active compound to a subject in need thereof.

Peptides and proteins, together called polypeptides, play a vital role in all biological processes and have received a growing attention in recent years as drug candidates. The rapid advances in peptide and protein pharmacology along with the large-scale production of these compounds by recombinant DNA technology—among other techniques— have fuelled enormous interest in these compounds. Unfortunately, peptide and protein development has far outpaced the ability to deliver these compounds systemically or locally using convenient and effective delivery systems.

Biodegradable polymers have received increased attention over the past decade for use in long-acting parenteral controlled release systems, either for systemic or site-specific drug delivery. Biodegradable controlled release formulations can significantly improve the pharmacokinetics of therapeutic compounds. This is especially relevant in the treatment of chronic diseases and for compounds with a narrow therapeutic window since systemic plasma concentrations can be reduced with concurrent reduction in undesirable side effects. Also many new biologically active compounds have short half-lives, necessitating frequent injection to achieve therapeutically effective plasma levels. Patient compliance and the high costs associated with frequent dosing regimens for parenterally administered biologically active compounds have increased the interest in biodegradable parenteral controlled release dosage forms.

Poly(D,L-lactic acid) (PDLLA) and copolymers of lactic acid and glycolic acid, also known as PLGA copolymers, are the most widely applied biodegradable polymers for use in parenteral controlled release depot formulations. PLGA copolymers have been successfully used for the development of sustained release depot formulations for small molecules, such as risperidone, and therapeutic peptides such as leuprolide, goserelin or octreotide.

PLGA polymers have, however, several drawbacks that limit their use and make them less suitable for the delivery of polypeptides. Firstly, PLGA copolymers are relatively hydrophobic polymers and do not provide an optimal environment for encapsulated proteins. Proteins may adsorb to the polymer, resulting in slow and incomplete release, protein unfolding and/or aggregation. Secondly, the ability to manipulate the release of larger biologically active compounds such as an encapsulated polypeptide is limited since diffusion of such compounds in the relatively rigid and non-swellable PLGA matrices is negligible. The release of proteins from PLGA copolymers therefore depends on diffusion via pores present in the matrix and on the degradation or dissolution time of the matrix. Typically, the encapsulated protein remains entrapped in the polymer matrix until the moment the latter has degraded to such an extent that it loses its integrity or dissolves, resulting in biphasic or triphasic degradation-dependent release profiles typically obtained for PLGA-based depot formulations. Finally, during degradation of PLGA copolymers, acidic moieties are formed that accumulate in the rigid and non-swellable PLGA matrix resulting in the formation of an acidic micro-environment in the polymer matrix with in situ pHs that can be as low as 1-2. Under such acidic conditions encapsulated proteins may form aggregates leading to incomplete protein release. Moreover, the low pH may have a deleterious effect on the structural integrity and biological activity of the encapsulated peptide or protein, potentially leading to reduced therapeutic efficacy and enhanced immunogenicity. Chemical modification of proteins and peptides, such as acylation and adduct formation have been reported.

Thus, there is a need for biodegradable polymers that are more suitable for protein delivery. However, one of the advantages of PLGA and related polymers is that they have a proven track record of clinical use and are generally considered as highly biocompatible, and as a consequence and because of risk mitigation reasons, have been adopted by pharmaceutical companies to develop depot formulations for their active compounds. It is therefore desired that a new biodegradable polymeric protein delivery system would be designed of polymers that are composed of monomers that are well-known, biologically safe and clinically acceptable.

In an attempt to provide a hydrophilic matrix with an improved compatibility for protein drugs that allows controlled release thereof, Kissel et al. (*J. Contr. Rel.* 1996, 39(2), 315-326) synthesised ABA triblock copolymers containing hydrophilic poly(ethylene oxide) B blocks and hydrophobic, biodegradable A blocks, consisting of poly(L-lactic-co-glycolic acid). Kissel et al. reported sustained release of various proteinaceous compounds from microspheres composed of poly(L-lactic-co-glycolic acid)-poly (ethylene glycol)-poly(L-lactic-co-glycolic acid) and poly (L-lactic acid)-poly(ethylene glycol)-poly(L-lactic acid) copolymers, i.e. ABA type polymers, where A is a hydrophobic block and B is polyethylene glycol. These copolymers are, however, limited in their A/B ratio, i.e. poly (ethylene glycol) (PEG) content. To prevent renal clearance issues associated with the use of high molecular weight PEG, the molecular weight of the PEG moiety used in these ABA triblock copolymers should preferably not exceed 5000 g/mol. Thus, to obtain high PEG content with the triblock polymers described by Kissel et al. while maintaining low PEG molecular weight, the hydrophobic blocks should also be short. This would yield polymers with undesirable properties for use as biomaterials, as at short block lengths glass transition temperature ($T_g$) is below room temperature (determined by the inventors) and crystallinity (in case of poly(L-lactic acid) (PLLA)) is very low or absent (De Jong, *Macromolecules,* 1998, 31(19), 6397-6402), thus yielding sticky materials and (too) fast and poorly controlled release of the incorporated active.

Examples of phase separated, segmented/block copolymers are found in e.g. U.S. Pat. Nos. 5,554,170, 5,066,772, 5,236,444, 5,133,739, and 4,429,080. These known materials are bioresorbable co-polyesters wherein the hard blocks are predominantly built of crystalline poly-glycolide and/or poly-lactide. These polymers are rigid and non-swellable and therefore suffer from the same disadvantages and limitations as mentioned for PLGA and PDLA making them unsuitable for the sustained release of proteins.

Biodegradable multi-block copolymers containing one hydrolysable polyester segment and one hydrophilic hydrolytically stable segment have been studied for their drug loading and release capacity (e.g. multi-block copolymers based on ε-caprolactone segments and poly(ethylene glycol) segments are described by Lee et al. (*J. Control. Rel.*, 2001, 73(2), 315-327). These polymers contain only one degradable segment, thus limiting the ability to control their degradation and release properties.

Known multi-block copolymers of two types of biodegradable pre-polymers (segments) on the other hand, can only be made in an alternating pre-polymer sequence, resulting in a limited range of possible variables (Penco et al., *J. Appl. Polym. Sci.* 2000, 78(10), 1721-1728).

Examples of biodegradable multi-block copolymers containing hydrolysable polyester segment of different composition are described in WO-A-2004/007588. These multi-block copolymers comprise biodegradable phase separated copolymers with segments of an amorphous, "soft", biodegradable pre-polymer (A) having a $T_g$ (glass transition temperature) below 37° C. and segments of a semi-crystalline, "hard", biodegradable pre-polymer (13) having a phase transition temperature of 40-100° C., in which the segments are linked by a multifunctional chain extender. To obtain multi-block copolymers with $T_m$ of 40-100° C. as disclosed in WO-A-2004/007588, the choice for pre-polymers to be used as B segments is limited to pre-polymers composed of either poly(s-caprolactone) (PCL) (WO-A-2004/007588), poly(valerolactone) (PVL) and/or polydioxanone (PDS). When PDS is used as segment B, multi-block copolymers with a $T_m$ of 80-90° C. (U.S. Pat. No. 5,711,958) are obtained. When PCL is used as segment B, multi-block copolymers with a $T_m$ of 40-60° C. (WO-A-2004/007588) are obtained. PVL homopolymers have a $T_m$ similar to PCL homopolymers (i.e. ~60° C.). Thus, when PVL would be used as segment B, multi-block copolymers with a $T_m$ of 40-60° C. would be obtained. PDS, PCL and PVL have relatively low $T_g$s of −10, −60 and −60° C., respectively. The low $T_g$ of the PDS, PCL and PVL segments limit the $T_g$ range of the multi-block copolymer (where the $T_g$ originates from phase mixing of the amorphous segment A and the amorphous part of the semi-crystalline segment B) that can be obtained and thus limit the control over release and degradation properties.

WO-A-99/02168 describes biodegradable multi-block copolymers for biomedical applications, where either ABA or AB type of pre-polymers are chain-extended. Chain-extension of either ABA of AB type of pre-polymers can only lead to alternating multi-block copolymers. An alternating block copolymer is represented by ABABABABAB in case of chain-extension of AB pre-polymers, or ABAABAABAABA in case of chain-extension of ABA pre-polymers.

Biodegradable phase separated multi-block copolymers containing a hard and a soft segment have been described in U.S. Pat. No. 6,160,084. This document describes the use of PCL-PLLA multi-block copolymers composed of pre-polymers that are linked with trimethylhexane-1,6-diisocyanate (THDI). These materials are mentioned to be useful in drug delivery systems where shape-memory is required. US-A-2006/0 140 999 describes the use of similar shape-memory polymers for use in drug release systems, wherein the shape-memory material comprises units, derived from monomers selected from the group consisting of caprolactone, lactide, glycolide and dioxanone. Examples include PDS-PCL and PDS-PLGA multi-block copolymers. These materials cannot exhibit any significant swelling capacity under (simulated) physiological conditions, since swelling would induce loss of mechanical properties and thus loss of the memorised shape.

Other phase-separated, segmented multi-block copolymers include polyetherester copolymers as described in U.S. Pat. No. 5,980,948. These copolymers consist of crystalline aromatic segments and soft PEG-containing segments linked by hydrolysable ester bonds. The copolymers have the inherent drawback that low swellable compositions, i.e. compositions rich in hydrophobic aromatic segments, are not well-degradable, due to the high crystallinity and hydrophobicity of the aromatic segments. Highly swellable compositions, i.e. compositions rich in PEG, are not well-degradable either, due to the low concentration of ester bonds. In contrast, the multi-block copolymers of the current invention are degradable at each segment A/segment B ratio, due to the presence of ester bonds in segment A as well as in segment B. Further, in contrast to the multi-block copolymers of the current invention, the $T_g$ of polyetherester copolymers cannot be varied and is always low, around the $T_g$ of PEG, i.e. −30° C.

Objective of the invention is to overcome one or more of the drawbacks observed in the prior art.

In a first aspect the invention is directed to a biodegradable, semi-crystalline phase separated, thermoplastic multi-block copolymer, the copolymer being characterised in that:
a) it comprises at least one hydrolysable pre-polymer (A) segment and at least one hydrolysable pre-polymer (B) segment;
b) said multi-block copolymer having a $T_g$ of 37° C. or less and a $T_m$ of 110-250° C. under physiological conditions;
c) the segments are linked by a multifunctional chain-extender;
d) the segments are randomly distributed over the polymer chain; and
d) at least part of pre-polymer (A) is derived from a water-soluble polymer.

The multi-block copolymer of the invention can be composed of at least two different segments each having different physical characteristics, including degradation and swelling characteristics. Due to their unique make-up and their semi-crystalline phase separated morphology, the materials of the invention are surprisingly versatile and extremely suited for constructing drug delivery matrices and drug eluting coatings, which are utilisable for encapsulating certain therapeutic agents and for sustained release of the encapsulated therapeutic agent either locally or into the systemic circulation. As is described herein below, the composition of the invention is of particular interest for the controlled release of a biologically active compound, such as a biologically active polypeptide to a host.

The term "phase-separated" as used herein is meant to refer to a system, in particular a copolymer, built of two or more different pre-polymers, of which at least two are (partially) incompatible with each other at body temperature or below (under physiological conditions such as in the human body). Thus the pre-polymers do not form a homogeneous mixture when combined, neither when combined as a physical mixture of the pre-polymers, nor when the pre-polymers are combined in a single chemical species as "chemical mixture", viz. as copolymer.

The term "pre-polymer" as used herein is meant to refer to the polymer segments that are randomly linked by a multi-functional chain extender, together making up the multi-block copolymer of the invention. Each pre-polymer may be obtained by polymerisation of suitable monomers, which monomers thus are the chemical units of each prepolymer. The desired properties of the pre-polymers and, by consequence, of the multi-block copolymer of the invention, can be controlled by choosing a pre-polymer of a suitable composition and molecular weight (in particular $M_n$), such that the required $T_m$ or $T_g$ is obtained.

The term "multi-block" as used herein is meant to refer to the presence of at least two distinct pre-polymer segments in a polymer chain.

The term "thermoplastic" as used herein is meant to refer to the non cross-linked nature of the multi-block copolymer. Upon heating, a thermoplastic polymer becomes fluid, whereas it solidifies upon (re-)cooling. Thermoplastic polymers are soluble in proper solvents.

The term "hydrolysable" as used herein is meant to refer to the ability of reacting with water upon which the molecule is cleaved. Hydrolysable groups include ester, carbonate, phosphazene, amide and urethane groups. Under physiological conditions, only ester, carbonate and phosphazene groups react with water in a reasonable time scale.

The term "multifunctional chain-extender" as used herein is meant to refer to the presence of at least two reactive groups on the chain-extender that allow chemically linking reactive pre-polymers thereby forming a multi-block copolymer.

The term "random multi-block copolymer" as used herein is meant to refer to a multi-block copolymer where the distinct segments are distributed randomly over the polymer chain.

The term "water-soluble polymer" as used herein is meant to refer to a polymer that has a good solubility in an aqueous medium, preferably water, under physiological conditions. This polymer, when copolymerised with more hydrophobic moieties, renders the resulting copolymer swellable in water. The water-soluble polymer can be derived from a diol, a diamine or a diacid. The diol or diacid is suitably used to initiate the ring-opening polymerisation of cyclic monomers.

The term "swellable" as used herein is meant to refer to the uptake of water by the polymer. The swelling ratio can be calculated by dividing the mass of the water-swollen copolymer by that of the dry copolymer.

The term "semi-crystalline" as used herein is meant to refer to a morphology of the multi-block copolymer that comprises two distinctive phases, an amorphous phase and a crystalline phase. Preferably, the multi-block copolymer is made up of an amorphous phase and a crystalline phase.

The term "biologically active compound" as used herein is intended to be broadly interpreted as any agent that provides a therapeutic or prophylactic effect. Such agents include, but are not limited to, antimicrobial agents (including antibacterial and antifungal agents), anti-viral agents, anti-tumour agents, hormones and immunogenic agents.

The term "biologically active polypeptide" as used herein is meant to refer to peptides and proteins that are biologically active in a mammal body, more in particular in the human body.

The semi-crystalline, phase separated multi-block copolymers of the invention overcome one or more of the aforementioned drawbacks and limitations. Due to the presence of segments derived from a water-soluble polymer (such as hydrophilic PEG segments), the phase separated multi-block copolymer swells in an aqueous environment to form a swollen hydrogel providing a natural environment for biologically active compounds such as proteins. When the multi-block copolymers of the invention are applied as a polymer matrix in a controlled release formulation for delivering a biologically active compound, the swellability of the multi-block copolymers can avoid accumulation in the polymer matrix of acidic degradation products formed during hydrolysis of the polymer chains. Instead, such degradation products are released from the matrix and thereby prevent the formation of an acidic micro-environment in the polymer matrix that would be deleterious to the encapsulated biologically active compound. Moreover, due to the swellability of the phase separated multi-block copolymers of the invention, any encapsulated compounds can be released gradually by diffusion thereby preventing the biphasic or triphasic release patterns typically obtained for non-swellable biodegradable polyesters such as poly(D,L-lactide) or poly(lactic-co-glycolic acid).

The multi-block copolymers of the invention have a $T_m$ of 110-250° C. under physiological conditions. This is due to the pre-polymer segment B. The segment B is based on crystallisable polymers, such as PLLA, poly(D-lactic acid) (PDLA), polyglycolic acid (PGA) or polyhydroxybutyrate (PHB), or combinations of crystallisable polymers. Most preferably, the segment B is based on a pre-polymer composed of PLLA. The amorphous phase of the phase separated multi-block copolymers of the invention predominantly consists of the soft A segments. Surprisingly, we have found that the amorphous part of the hard segments B also contribute to the total amorphous phase of the multi-block copolymers of this invention.

For multi-block copolymers described in WO-A-2004/007588 the choice for pre-polymers to be used as B segments is limited to pre-polymers composed of poly(ε-caprolactone) (PCL), poly(valerolactone) (PVL) and poly(dioxanone) (PDS) due to the $T_m$ of pre-polymer (B) being in the range of 40-100° C. (regarding common polyesters used for biomedical applications). In accordance with the invention, the $T_m$ of pre-polymer (B) is preferably in the range of 110-250° C. As a result, pre-polymer (B) can be selected from a list of chemically different pre-polymers that were not previously considered. The inventors found that the different chemistry for pre-polymer (B) yields multi-block copolymers that exhibit advantageous properties which cannot be obtained with the copolymers described in WO-A-2004/007588.

When PDS is used as segment B, multi-block copolymers with a $T_m$ of 80-90° C. (U.S. Pat. No. 5,711,958) are obtained. When PCL is used as segment B, multi-block copolymers with a $T_m$ of 40-60° C. (U.S. Pat. No. 5,711,958) are obtained. PVL homopolymer has a $T_m$ of approximately 60° C., similar to PCL homopolymer. When PVL segments are used as segment B, multi-block copolymers with a $T_m$ of approximately 40-60° C. are obtained. PDS, PCL and PVL are semi-crystalline, and thus possess a $T_g$ in addition to their $T_m$. PDS, PCL and PVL all possess a low $T_g$ of their respective amorphous phases of approximately −10° C., −60° C. and −70° C., respectively. Increasing the temperature range for block B to 110-250° C. opens up the possibility to use PLLA, PDLA, PGA and PHB. These polymers have a higher $T_g$ of approximately 50° C., 35° C. and 0° C., respectively. Irrespective of which polymer is used for the hard B segments, these hard B segments will always be semi-crystalline by themselves, i.e. partly amorphous. Surprisingly, it was found that the amorphous part of the hard B segments will (partly) phase mix with the soft A segments and thus both will contribute to the overall $T_g$ of the multi-block copolymer. Therefore, the $T_g$ of the amorphous phase is determined by both the $T_g$ of segment A and the $T_g$ of segment B, in combination with the molar ratio of segment A/B. The $T_g$ can be varied from $T_g$ close to pre-polymer (A) (when pre-polymer A/B ratio of close to 1 is used) to $T_g$ close to pre-polymer B (when pre-polymer A/B ratio close to zero is used). Importantly, the release of actives encapsulated in the polymer matrix depends heavily on the $T_g$ of the amorphous phase, as the diffusion of actives occurs through the amorphous phase and not the dense, crystalline phase. Also, the degradation rate of a polymer depends heavily on the $T_g$ of the amorphous phase, as this influences the rate of water influx and thus the rate of hydrolysis. The use of pre-polymer (B) with $T_m$ 110-250° C. having relatively high $T_g$ enables covering a much broader $T_g$ range than would have been possible with pre-polymer (B) having $T_m$ 40-100° C. and a relatively low $T_g$. As a consequence, the using such pre-polymers (B) for preparing multi-block copolymers with a $T_m$ in the range of 110-250° C. enables a much broader range of release and degradation properties of the polymer and thus also allows better control over the release of different biologically active compounds.

Furthermore, the higher $T_m$ of the multi-block copolymers of the current invention allows the preparation of non-sticky microspheres by a double-emulsion process at ambient conditions, while still having short B segments. The limitation of the length of the crystallisable B segment is important to have multi-block copolymers that degrade well under physiological conditions, contrary to higher molecular weight crystalline PLLA polymers. In contrast, microspheres cannot be made using multi-block copolymers where segment B is composed of a short PCL since the short PCL blocks do not form crystalline domains during microsphere formation. As a consequence the polymer remains amorphous. Due to the low $T_g$ of the amorphous polymer, the polymer is sticky due to which microspheres agglomerate and fuse together during the extraction/evaporation process step. Since PVL has a similar $T_m$ as PCL, it is to be expected that microspheres cannot be made using multi-block copolymers where segment B is composed of a short PVL pre-polymer. No reference has been made in literature of microspheres composed of PDS or PDS copolymers. It is known from literature that crystallisation of PDS is slow and incomplete at fast cooling rates and/or low PDS molecular weight. These results predict that preparation of microspheres by a double-emulsion process using multi-block copolymers with segment B being a short PDS block is not feasible.

Theoretically, the storage stability of microspheres at ambient conditions made with pre-polymer (B) having $T_m$ 110-250° C. is improved compared to pre polymer (B) having $T_m$ 40-100° C. Increased $T_m$ increases the $T_c$ and thus increases the crystallinity of the microspheres. A higher crystallinity will reduce the molecular mobility of the encapsulated biologically active compound in the polymer matrix and improve the storage stability of the product. It is known from literature that increased crystallinity increases the storage stability of particles. Also, pre-polymers B having $T_m$ 110-250° C. have higher $T_g$ compared to pre-polymers (B) having $T_m$ 40-100° C. It is known from literature that for semi-crystalline as well as amorphous particles, increased $T_g$ increases the storage stability.

The multi-block copolymers of the invention further have an improved degradation rate compared to multi-block copolymers where the crystallisable segment is based on PCL, because the B segments in the multi-block copolymers of the invention are less hydrophobic compared to PCL.

Synthesis of multi-block copolymers where the crystallisable segment is based on PDS is hampered by the limited polymerisation of the PDS monomer, p-dioxanone and the limited solubility of PDS in common solvents. It is well known that p-dioxanone has a relatively low ceiling temperature, leading to maximum conversion of approximately 80%. In contrast, monomers used for the multi-block copolymers of the invention, such as lactide and glycolide, can be easily polymerised to conversions above 95%. The limited solubility of PDS containing polymers also limits their use for preparation of controlled release formulations.

Multi-block copolymers of this invention that are composed of a PLLA-based segment B have the additional advantage that PDLA may be added as an additional B segment, yielding multi-block copolymers with increased crystallinity and decreased degradation rate due to the formation of PLLA/PDLA stereocomplex crystals with a $T_m$ as high as 220° C., which is approximately 50° C. higher than the $T_m$ of crystalline PLLA segments that are solely composed of enantiomer L-lactide.

In the multi-block copolymers of the invention, the content of the segments derived from a water-soluble polymer may be varied independently from the block length of the hydrophobic (crystalline) segment. Therefore, high contents of segments that are derived from a water-soluble polymer can be obtained, while maintaining crystallinity. Furthermore, the intrinsic viscosity (IV) of the multi-block copolymers of the invention may be varied independently from the composition, in contrast to the ABA triblock copolymers described by Kissel et al. The high degree of variability of the multi-block copolymers of the invention allows easy tuning of the length, ratio and composition of the segments to obtain the desired degradation characteristics and drug release kinetics.

The multi-block copolymers of this invention further have advantages over the block copolymers of structure ABA as mentioned in the examples of the introduction. Although polymer properties can be greatly improved by using block copolymers with blocks of different copolymers instead of homo or random copolymers, these ABA copolymers still have certain disadvantages.

To obtain a minimum molecular weight of the ABA copolymer, the sequences A and B must have a certain length. The blocks may independently behave as the individual homopolymers with similar composition. Properties of the ABA type copolymers can only be tuned by varying the composition of A and B blocks. Another disadvantage is that block copolymers must be prepared at relatively high temperatures (>100° C.) under inert conditions for complete conversion of all the monomers and to obtain sufficient molecular weight. The first disadvantage can be solved by using multi-block copolymers wherein the blocks or segments are much shorter and linked together by a chemical reaction performed at temperatures below 100° C. Properties such as degradation behaviour can be tuned in a much better way by choosing the proper combination of segment lengths, ratio and composition.

Furthermore, due to the relatively high temperatures used in the process of preparing ABA block copolymers (and derivatives thereof), there is always a possibility of transesterification, resulting in a certain extent of phase mixing. The multi-block copolymers of the invention do not suffer from this disadvantage since they can be prepared by linking pre-polymers with previously determined monomer composition at rather low temperatures (<100° C.) thus avoiding transesterification and other side-reactions reactions, which may cause the generation of undesired degradation and other by-products. This means that the monomer sequence length of the copolymer is determined by the choice of building components and not so much by reaction time and temperature, as being usually applied for synthesis of random copolymers. Another advantage of multi-block copolymers of this invention prepared by linking of pre-polymers using a multifunctional chain-extender is that the pre-polymer segments are randomly distributed in the copolymer, thus offering much more possibilities of tuning the properties. A random multi-block copolymer is for example ABBBBA-BAAABBAAAAA . . . etc. The random multi-block copolymers of the invention provide many advantages that cannot be obtained with alternating multi-block copolymers.

Firstly, the random multi-block copolymers obtained by chain extension of A and B blocks have an unlimited A to B ratio. A:B can, for instance, be 10:90, but may as well be 90:10. In contrast, the ratio of the blocks in an alternating multi-block copolymer is limited to the ratio used in the chain extended polymer. For instance, in the case of chain extension of AB the A:B ratio in the multi-block copolymer is 50:50. The random nature of the multi-block copolymers of the invention greatly increases the possible compositions of the material and thereby the control over its physical and chemical properties. This includes a better control of the swelling capacity in water, morphology (phase separation, amorphous/crystallinity) and polymer degradation.

Secondly, the synthesis method of the random multi-block copolymers of the invention is much less laborious as compared to the synthesis of alternating multi-block copolymers. In alternating multi-block copolymers either segments A and B in case of AB diblocks, or segments A and C in case of ACA triblocks, have to be linked prior to chain-extension (or a macro chain-extender needs to be synthesised). In random multi-block copolymers, separate A and B blocks are chain extended with e.g. a commercially available chain-extender.

Another advantage of the multi-block copolymers of the invention is that they are based on a multifunctional (preferably aliphatic) chain-extender. By choosing the type and amount of chain-extender the polymers properties can be affected (for instance, the chain-extender may act as a softener or it may affect the degree of phase separation). The total degree of freedom to obtain polymers with the desired properties is therefore increased compared to polymers of the prior art.

In accordance with the invention phase separated multi-block copolymers are provided that swell sufficiently in an aqueous environment and under physiological conditions upon administration so as to provide an aqueous microenvironment for the encapsulated peptide or protein and allow diffusion controlled release of the peptides and proteins. The materials thus show a significant decrease of the mechanical strength. Although such materials can be used as shape-memory materials under dry conditions without showing a significant decrease in mechanical strength prior to the transition to the memorised shape, e.g. by means of using temperature or light as an external trigger, these materials do show significant dimensional changes and a significant decrease of their mechanical strength under hydrated conditions, simply because these materials absorb significant amounts of water due to their hydrophilic character leading to extensive swelling and plasticisation of the material. As a consequence, under hydrated conditions, such as the physiological conditions encountered in a human or animal body, the size of constructs prepared of these materials changes significantly and the mechanical properties of these materials change orders of magnitude. Contrary to the multi-block copolymers of the current invention, the shape-memory materials described in U.S. Pat. No. 5,711,958 hardly swell under hydrated conditions, such as the physiological conditions encountered in a human or animal body.

Phase separated polyesters or polyester-carbonates of this invention are a promising group of biomaterials and can be used in various drug delivery applications since they provide excellent control over drug release and allow release of biologically active compounds, such as polypeptides.

The morphology of the multi-block copolymer (or of a construct made thereof) is dependent on the environmental conditions: a DSC (Differential Scanning calorimetry) measurement may be performed under inert (dry) conditions and the results may be used to determine the dry materials' thermal properties. However, the morphology and properties under physiological conditions (i.e., in the body) may be different from the morphology and properties under ambient conditions (dry, room temperature). It is to be understood that the transition temperatures, $T_g$ and $T_m$ as used herein, refer to the corresponding values of a material when applied in vivo; viz. when at equilibrium with an atmosphere that is saturated with water vapour and at body temperature. This may be simulated in vitro by performing the DSC measurement after allowing the material to equilibrate with a water-saturated atmosphere. When in dry state, the materials used in the invention may have $T_g$ values that are somewhat higher than at mammalian body conditions, that is to say, when the dry materials are subjected to DSC, the first inflection point may arise at higher temperatures, for instance at 42° C. or 50° C., or more. Upon application in vivo, however, the dry material's $T_g$ and/or $T_m$ will drop as a result of the absorption of water, which plasticises the polymer and this final $T_g$ should be around body temperature or lower according to the invention. The final $T_m$ should be present at temperatures between 110° C. and 250° C. under physiological conditions.

For instance, a polymer that contains PEG in the soft segment can be crystalline under dry conditions at ambient temperature, while amorphous under wet conditions, giving a mixed $T_g$ or two separated $T_g$s of the soft segment formed by amorphous softened PEG and the polyester/carbonate. The phase separated character of the copolymers of the invention is reflected in the profile of the $T_g$ or $T_m$. The phase separated copolymers are characterised by at least two phase transitions, each of which is related to (but in general not identical to) the corresponding $T_g$ or $T_m$ values of the pre-polymers which are comprised in the copolymer. The $T_g$ is determined by taking the midpoint of the specific heat jump, as may be measured e.g. by DSC. The $T_m$ is the peak maximum of the melting peak, as is schematically illustrated in FIG. 1, that shows the heat flow endotherm for a copolymer characterised by a $T_g$ and a $T_m$. As defined herein, values of $T_g$ and $T_m$ of a certain pre-polymer reflect the values as measured on the copolymer. In case of complete immiscibility of the pre-polymers, the $T_g$ of the copolymer is governed solely by the $T_g$ of the amorphous, "soft" pre-polymer. In practice, however, the composition of the crystalline and amorphous phase of the multi-block copolymer is not the same as the composition of the soft A segments and the semi-crystalline B segments. The amorphous part of the original hard segment forming pre-polymer will mix with the soft segment forming pre-polymer (A) and thus become part of the amorphous phase. The $T_g$ value of the amorphous phase is then different from that of the pre-polymer used. The extent of miscibility (and therefore the deviation of $T_g$ and/or $T_m$ from those of the corresponding pre-polymers) is dependent on the pre-polymer composition, ratio and segment length in the copolymer. The $T_g$ of the copolymer segments generally lies between the $T_g$ value of the phase mixed copolymer and the $T_g$ value of the separate pre-polymers.

The physicochemical properties (such as degradation, swelling and thermal properties) of the multi-block copolymers can be easily tuned by changing the type of monomers of the soft and hard segment forming pre-polymers and their chain length and chain ratio and by choosing the type and amount of chain-extender. Furthermore, the phase transition temperatures are low enough for processing the polymer in the melt. The monomer ratio and distribution of the copolymer can be easily controlled by varying the polymerisation conditions.

A crystalline segment B is usually desired to obtain non-sticky materials. Also, the phase separated morphology, with amorphous and crystalline domains, must be maintained during exposure to physiological conditions (i.e. an aqueous environment at body temperature) in order to have controlled swelling of the polymer matrix. Control over the swelling degree is essential to control the release of encapsulated compounds. The crystalline B segments act as physical cross-links that control the swelling of the more hydrophilic soft segments. Besides being affected by the content of hard segment B, the swelling degree of the polymers depends on the content and molecular weight/length of water-soluble polymer in the soft A segment.

As mentioned previously, a prerequisite of the phase separated segmented co-polyester is that the $T_m$ of the polyester segment B is in the range of 110-250° C. and the $T_g$ of the segment A is below 37° C. under physiological conditions. The $T_m$ of segment B in the multi-block copolymer will in general be lower than that of the non-reacted pre-polymer (B) due to decreased chain flexibility once the pre-polymer is built in in the multi-block copolymer and due to possible phase mixing of other components of the multi-block copolymer in the crystalline phase. An important class of segmented co-polyesters with good phase separation are those based on hard segments B composed of crystalline PLLA. The inventors have shown that multi-block copolymers with PLLA-based B segments have $T_m$ of at least 110° C. under physiological conditions. These multi-block copolymers offer several advantages. A wide range of degradation rate can be obtained. Pre-polymer (B) that forms the hard segment B is based on crystalline PLLA and such polymers are known to degrade very slowly. In contrast, pre-polymer (A) is a polymer that is based on a water-soluble polymer and amorphous polyester. Such polymers are known to degrade relatively fast. The final degradation rate is determined by the segment A/segment B ratio and can thus be easily tuned. Since release is among others governed by the degradation rate of the multi-block copolymer, this can also be tuned by the segment A/segment B ratio. Also, the crystallinity can easily be increased by mixing PLLA with PDLA to form a stereocomplex. The stereocomplexation leads to higher crystallinity compared to the single enantiomer and also to higher $T_m$ (~50° C. higher than the single enantiomer). Furthermore, the $T_g$ of multi-block copolymers with PLLA-based B segments can be varied in a wide range, from about −40 up to 40° C. (measured under dry conditions). Since degradation rate and release rate are, among others, governed by $T_g$ of the matrix, this wide $T_g$ range also offers great tuning of the release and degradation properties.

Generally, the desired phase separated morphology (reflected by one melting point and at least one low $T_g$ value) may be obtained by varying the composition, e.g. by choosing the number average molecular weight, $M_n$, of the A and B pre-polymers. It is also possible to influence the phase separated morphology by varying the segment A/segment B ratio.

The segmented multi-block copolymers of this invention comprise a soft segment A derived from pre-polymer (A) which is hydrolysable and typically completely amorphous at physiological (body) conditions. Furthermore, pre-polymer (A) preferably has at least one phase transition being a $T_g$ of 37° C. or less, preferably 25° C. or less as measured under physiological (body) conditions. This segment will be part of the amorphous phase in the multi-block copolymer, wherein the amorphous phase is referred herein as phase (A). The copolymers of the invention also comprise a hard segment B derived from pre-polymer (B), comprising a semi-crystalline, hydrolysable polymer typically with a $T_m$ of 110-250° C. as measured at physiological (body) conditions. Segment B mostly contributes to phase (B). The pre-polymers A and B that form the "soft" and "hard" segments, respectively, are linked by a multifunctional chain-extender. Typically, the crystalline phase(s) is (are) comprised of hard segments B and the amorphous phase(s) is (are) comprised of soft segments A and the amorphous part of segments B. The crystalline and amorphous phase(s) is (are) incompatible or only partially compatible at body conditions, viz. they phase separate. The multifunctional chain-extender is preferably an aliphatic molecule.

The resulting multi-block copolymers of the invention preferably have a structure according to formula (1):

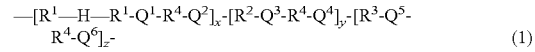
$$—[R^1—H—R^1-Q^1-R^4-Q^2]_x-[R^2-Q^3-R^4-Q^4]_y-[R^3-Q^5-R^4-Q^6]_z- \quad (1)$$

wherein $R^1$ is part of segment A, which is part of phase (A), and may be amorphous polyester, amorphous polyetherester or amorphous polycarbonate; or an amorphous pre-polymer that is obtained from combined ester, ether and/or carbonate groups. H is the middle block of segment A and is derived from a water-soluble polymer. The block derived from the water-soluble polymer may be amorphous or semi-crystalline at room temperature. However, block H thus introduced in segment A will become amorphous at physiological conditions. This water-soluble polymer is selected from the group consisting of polyethers such as polyethylene glycol (PEG), polytetramethyleneoxide (PTMO) and polypropyleneglycol (PPG); polyvinylalcohol (PVA) polyvinylpyrrolidone (PVP), polyvinylcaprolactam, poly(hydroxyethylmethacrylate) (poly-(HEMA)), polyphosphazenes, polyorthoesters, polyorthoesteramides or copolymers of the previous polymers. Preferably, H is PEG, which is the initiator of the ring-opening polymerisation of a cyclic monomer that forms $R^1$.

$R^2$ is segment B and mainly or entirely contributes to phase (B). $R^2$ may be a crystalline or semi-crystalline polyester, polyetherester, polycarbonate or polyanhydride; or pre-polymers of combined ester, ether, anhydride and/or carbonate groups. It is possible that part of phase $R^2$ is amorphous, in which case this part of $R^2$ will contribute to phase (A). $R^1$ and $R^2$ are preferably not the same. The variable z is zero or a positive integer. Variables x and y are both a positive integer.

Optionally, segment $R^3$ is present. This segment is derived from a water-soluble polymer that is chosen from the group of polymers mentioned for H. $R^3$ will be part of the amorphous phase (A) under physiological conditions. If $R^3$ is present then the multi-block copolymer of the invention comprises a water-soluble polymer as an additional pre-polymer. Preferably, this water-soluble polymer is selected from the group consisting of polyethers such as polyethylene glycol (PEG), polytetramethyleneoxide (PTMO) and polypropyleneglycol (PPG); polyvinylalcohol (PVA) polyvinylpyrrolidone (PVP), polyvinylcarprolactam, poly(hydroxymethylmethacrylate) (poly-(HEMA)), polyphosphazenes, polyorthoesters, polyorthoesteramides or copolymers of the previous polymers. For example, the said water-soluble polymeric segment is derived from PEG having a $M_n$ of 150-5000 g/mol.

$R^4$ is derived from the chain-extender and consists of an aliphatic $C_2$-$C_8$ alkylene group, optionally substituted by a $C_1$-$C_{10}$ alkylene, the aliphatic group being linear or cyclic. $R^4$ is preferably a butylene, —$(CH_2)_4$—, group. The $C_1$-$C_{10}$ alkylene side group may contain protected S, N, P or O moieties. Chain-extenders containing aromatic groups are generally not suitable, since chain-extenders containing aromatic groups may give rise to undesired degradation products. Therefore, aliphatic chain-extenders are preferred.

$Q^1$-$Q^6$ are linking units obtained by the reaction of the pre-polymers with the multifunctional chain-extender. Each of $Q^1$-$Q^6$ may be independently selected from amine, urethane, amide, carbonate, ester and anhydride. The event that all linking groups Q are different is rare and usually not preferred.

Typically, one type of chain-extender may be used with three pre-polymers having the same end-groups resulting in a copolymer of formula (1) with six similar linking groups.

In case pre-polymers $R^1$ and $R^2$ are differently terminated, two types of groups Q will be present: e.g. $Q^1$ and $Q^2$ will be the same between two linked segments $R^1$, but $Q^1$ and $Q^2$ are different when $R^1$ and $R^2$ are linked. The examples of formula (1) show the result of the reaction with a difunctional chain-extender and difunctional pre-polymers.

With reference to formula (1) the polyesters of the invention may also be represented as multi-block or segmented copolymers having a random distribution of segments $(AB)_r$, wherein 'A' corresponds to the segment A and 'B' corresponds to the segment B (for z=0). In $(AB)_r$, the A/B ratio (corresponding to x/y in formula (1)) may be unity or away from unity. The pre-polymers can be mixed in any desired amount and can be coupled by a multifunctional chain-extender, viz. a compound having at least two functional groups by which it can be used to chemically link the pre-polymers. Preferably, this is a difunctional chain-extender. In case z≠0, then the presentation of a random distribution of all the segments can be given by $(ABC)_r$, were three different pre-polymers (one being a segment derived from a water-soluble polymer such as PEG) are randomly distributed in all possible ratios.

The pre-polymers of which the a and b (and optionally c) segments are formed in $(AB)_r$, and $(ABC)_r$ are linked by the multifunctional chain-extender. This chain-extender is preferably a diisocyanate chain-extender, but can also be a diacid or diol compound. In case the pre-polymers all contain hydroxyl end-groups and a diisocyanate chain-extender is used, the linking units will be urethane groups. In case (one of) the pre-polymers (is) are carboxylic acid terminated, the linking units are amide groups. Multi-block copolymers with structure $(AB)_r$, and $(ABC)_r$ can also be prepared by reaction of di-carboxylic acid terminated pre-polymers with a diol chain-extender or vice versa (diol terminated pre-polymer with diacid chain-extender) using a coupling agent such as DCC (dicyclohexyl carbodiimide) forming ester linkages.

As mentioned above, randomly segmented copolymers refer to copolymers that have a random distribution (i.e. not alternating) of the segments A and B. In case of segments A and B this can be represented by $(AB)_r$, in case of segments A, B and C this can be represented by $(ABC)_r$.

The hydrolysable segment $R^1$—H—$R^1$ of formula (1) is obtained by reaction of pre-polymer (A).

Pre-polymer (A) may e.g. be prepared by ring-opening polymerisation. Thus a pre-polymer (A) may be a hydrolysable copolymer prepared by ring-opening polymerisation initiated by a diol or diacid compound, preferably having a random monomer distribution. The diol compound is preferably an aliphatic diol or a low molecular weight polyether such as PEG. The polyether is part of the pre-polymer (A) by using it as an initiator and it can additionally be mixed with the pre-polymer (A), thus forming an additional hydrophilic segment $R^3$ in formula (1). Pre-polymer (A) may be a hydrolysable polyester, polyetherester, polycarbonate, polyestercarbonate, polyanhydride or copolymers thereof. For example, pre-polymer (A) comprises reaction products of ester forming monomers selected from diols, dicarboxylic acids and hydroxycarboxylic acids. Pre-polymer (A) may comprise reaction products of cyclic monomers and/or non cyclic monomers. Exemplary cyclic monomers include glycolide, lactide, ε-caprolactone, δ-valerolactone, trimethylene carbonate, tetramethylene carbonate, 1,5-dioxepane-2-one, 1,4-dioxane-2-one (para-dioxanone) and/or cyclic anhydrides such as oxepane-2,7-dione. In one embodiment, L-lactide, D-lactide and/or D,L-lactide is used.

To fulfil the requirement of a $T_g$ below 37° C., some of the above-mentioned monomers or combinations of monomers are more preferred than others. For example, pre-polymer (A) containing the monomers lactide and/or glycolide is preferably combined with any of the other mentioned cyclic co-monomers (ε-caprolactone, δ-valerolactone, trimethylenecarbonate, 1,4-dioxane-2-one and combinations thereof). This may by itself lower the $T_g$. Alternatively, the pre-polymer is initiated with a PEG with sufficient molecular weight to lower the $T_g$ of the multi-block copolymer.

In case pre-polymer A contains poly(D,L-lactide), the L/D ratio of the lactide may be away from unity (other than 50/50). For instance, an L/D ratio between 85/15 and 15/85 gives a completely amorphous homo-polymer. Furthermore, it is known that an excess of one isomer (L or D) over the other increases the $T_g$ of the poly(D,L-lactide). A minor amount of any other of the above mentioned monomers that build the amorphous phase may also be present in the crystalline phase forming pre-polymer or block.

Furthermore, pre-polymer (A) can be based on (mixtures of) condensation (non-cyclic) type of monomers such as hydroxyacids (e.g. lactic acid, glycolic acid, hydroxybutyric acid), diacids (e.g. glutaric, adipic or succinic acid, sebacic acid) and diols such as ethylene glycol, diethylene glycol, 1,4-butanediol or 1,6-hexanediol, forming ester and/or anhydride hydrolysable moieties.

The segment $R^2$ of formula (1) may be obtained by reaction of pre-polymers (B) derived from monomers L-lactide, D-lactide, hydroxybutyrate, glycolide or a combination of these monomers resulting in stereocomplex formation, having a phase transition between 110° C. and 250° C. under physiological conditions Preferably, segment B is obtained by reaction of L-lactide monomer.

Typically, pre-polymer (B) has an $M_n$ of 1000 g/mol or more, preferably 2000 g/mol or more, more preferably 3000 g/mol or more. In general, $M_n$ of pre-polymer (B) will 10 000 g/mol or less. The content of pre-polymer (B) in the copolymer is preferably 10-90 wt. % based on total weight of the multi-block copolymer, more preferably 25-70 wt. %, most preferably 30-50 wt. %.

The pre-polymers will preferably be linear and random (co)polyesters, polyester-carbonates, polyetheresters, or polyanhydrides with reactive end-groups. These end-groups may be hydroxyl or carboxyl. It is preferred to have a dihydroxy terminated copolymer, but hydroxy-carboxyl or dicarboxyl terminated polymers can also be used. In case the polymer has to be linear, it can be prepared with a difunctional component (diol) as a starter, but in case a three or higher functional polyol is used, star shaped polyesters may be obtained. The diol in pre-polymer (A) can be an aliphatic diol or a low molecular weight polyether.

The pre-polymer synthesis by a ring-opening polymerisation is preferably carried out in the presence of a catalyst. A suitable catalyst is $Sn(Oct)_2$ with M/I=5000-30 000 (M/I is the monomer to initiator ratio). It is also possible to carry out the synthesis without a catalyst.

The conditions for preparing the polyesters, polycarbonates and polyanhydrides are those known in the art.

The copolymers of the invention are generally linear. However, it is also possible to prepare the copolymers in a branched form. These non-linear copolymers of the invention may be obtained by using a trifunctional (or higher functional) chain-extender, such as tri-isocyanate. Branched copolymers may show improved creep characteristics.

For the crystallisable hard segment, the length ($M_n$) of the pre-polymer must be large enough to be able to crystallise in the copolymer. For example, PLLA hard segment forming pre-polymer preferably has a $M_n$ of 700 g/mol or more, more preferably 2000 g/mol or more, most preferably 3000 g/mol or more. A larger PLLA pre-polymer length is expected to result in a phase separated morphology at a lower hard segment content. The pre-polymer ratio at which phase separation is observed is therefore dependent on the pre-polymer lengths. In general, the lengths of the pre-polymers that form the soft and hard segment within a copolymer must have a value at which a phase separated morphology is observed, the extent of phase separation (incompatibility) being favourable for the desired properties of the biomedical device.

The soft segment forming pre-polymer (A) can have an $M_n$ of 500 g/mol or more, preferably 1000 g/mol or more, more preferably 2000 g/mol or more. The length of the pre-polymers must be chosen in such a way that they are as large as is necessary to obtain a good phase separated morphology and good mechanical and thermal properties of the resulting copolymer. The pre-polymer length must be low enough to be miscible with the chain-extender at the polymerisation temperature. Typically, this is achieved when $M_n$ is 10 000 g/mol or less.

Generally, a hard segment content in the range of 10-90 wt. % based on total weight of the multi-block copolymer, preferably of 25-90 wt. %, results in flexible, thermoplastic materials with good degradation and swelling properties at the temperature of application (viz. about 37° C. for medical applications).

In a further aspect the invention is directed to a process for preparing the phase separated, thermoplastic multi-block copolymers of the invention, comprising a chain-extension reaction of pre-polymer (A) and pre-polymer (B) in the presence of a multifunctional chain-extender, thereby obtaining a randomly segmented multi-block copolymer.

Segmented multi-block copolymers with structure $(AB)_r$ and $(ABC)_r$ can be made by chain-extending a mixture of the pre-polymers, containing the hard and the soft segments forming monomers of segments $R^1$, H and $R^2$, and optionally $R^3$, in the desired ratio with an equivalent amount of a multifunctional chain-extender, preferably an aliphatic molecule, more preferably a diisocyanate such as 1,4-butanediisocyanate (BDI). The segmented copolymers of structures $(AB)_r$ or $(ABC)_r$ are preferably made in solution. Suitably, the pre-polymer(s) are dissolved in an inert organic solvent and the chain-extender is added pure or in solution. The polymerisation temperature can be the same or even lower than the highest phase transition temperature of the pre-polymers. Coupling reactions with dicyclohexyl carbodiimide (DCC) are preferably carried out in solution. Two (or three) pre-polymers that are all diol or diacid terminated may be mixed in solution with a diacid or diol terminated chain-extender, respectively, after which DCC is added.

Polymerisation takes place for a time long enough to obtain an intrinsic viscosity of the copolymer of 0.1 dl/g or higher (measured at 25° C. in chloroform). The low polymerisation temperature and short polymerisation time will prevent from transesterification so that the phase separated morphology is obtained and the monomer distribution is the same as in the pre-polymers that build the copolymer. On the contrary, high molecular weight random copolymers have to be prepared at higher temperatures (>100° C.) and for a much longer time to obtain a full incorporation of all the monomers. During that time transesterification reactions will occur and a more random (i.e. less blocky) monomer distribution is obtained.

The materials obtained by chain-extending in the bulk can also be produced in situ in an extruder.

If the chain-extender is a difunctional, aliphatic molecule and the pre-polymers are linear, a linear copolymer is made; if one of the reactants (either the chain-extender or at least one of the pre-polymers) or both have more than two functional groups, branched structures may be obtained at sufficiently low conversion. The chain-extender can be a difunctional aliphatic chain-extender, preferably a diisocyanate such as 1,4-butanediisocyanate.

The combination of crystalline and amorphous phase forming pre-polymers or monomers is chosen in such a way to obtain a phase separated segmented or block co-polyester or polyester-carbonate with the desirable degradation, swelling, physical and thermal properties. Typically, the intrinsic viscosity is larger than 0.1 dl/g and less than 10 dl/g (measured at 25° C. in chloroform), preferably between 0.1-2 dl/g, and more preferably between 0.2-1 dl/g.

The multi-block segmented copolymers can be formed into formulations of various shape and dimensions using any known technique such as, for example, emulsification processes, extrusion, moulding, solvent casting, spray-drying, spray-freeze drying, electrospinning, or freeze drying. The latter technique is used to form porous materials. Porosity can be tuned by addition of co-solvents, non-solvents and/or leachables. Copolymers can be processed (either solid or porous) into microspheres, microparticles, nanospheres, rods, films, sheets, sprays, tubes, membranes, meshes, fibres, plugs, coatings and other articles. Products can be either solid, hollow or (micro)porous. A wide range of biomedical implants can be manufactured for applications in for example wound care, skin recovery, nerve regeneration, vascular prostheses, drug delivery, meniscus reconstruction, tissue engineering, coating of surgical devices, ligament and tendon regeneration, dental and orthopaedic repair. The copolymers can be used alone or can be blended and/or co-extruded with other absorbable or non-absorbable polymers.

Furthermore, they can be used in pharmaceutical applications, e.g. for drug delivery, e.g. in the form of microspheres, solid implants, gels, coatings, films, sheets, sprays, tubes, membranes, meshes, fibres, plugs, and other configurations.

As will be illustrated in the examples below, the materials of the invention have improved properties, including thermal, mechanical, processing compared to copolymers described in the prior art.

In yet a further aspect, the invention is directed to a composition for the delivery of at least one biologically active compound (e.g. a biologically active small molecule, protein or peptide) to a host, comprising the at least one biologically active compound encapsulated in a matrix, wherein said matrix comprises at least one phase separated, thermoplastic multi-block copolymer as defined herein.

It was found that a biodegradable multi-block copolymer of the invention is particularly suitable as delivery vehicle for a polypeptide, allowing for the controlled release of the polypeptide from the matrix into its environment, e.g. in the body of a subject.

The multi-block copolymers of the invention have many options for tuning the release properties of the delivery composition for the specific application. The release rate of the biologically active compound may for example be increased by:
  increasing the molecular weight of the water-soluble polymer in pre-polymer (A) at constant molecular weight of pre-polymer (A);
  increasing the molar ratio between pre-polymer (A) and pre-polymer (B);
  increasing the content of a monomer that gives a faster degrading polymer in pre-polymer (A), e.g. by replacing ε-caprolactone by D,L-lactide or glycolide or by replacing D,L-lactide with glycolide;
  decreasing the molecular weight of pre-polymer (B) at a constant molar ratio between pre-polymer (A) and pre-polymer (B) (this increases the pre-polymer (A) weight percentage and also decreases the $T_m$ of pre-polymer (B) and the total amount of crystalline phase present);
  decreasing the molecular weight of pre-polymer (A) at a constant molecular weight of the water-soluble polymer and molar ratio between pre-polymer (A) and pre-polymer (B); and/or
  the use of an additional, third segment derived from a water-soluble polymer, whereby the content of the water-soluble polymer is increased.

The release rate may be decreased by the opposite changes as mentioned above, as well as by
  increasing the $T_m$ of segment B, e.g. by the use of a mixture of PLLA and PDLA as pre-polymer (B) (instead of only PLLA) in a ratio such that stereocomplexation occurs between PLLA and PDLA;
  the use of an additional, third segment derived from a water-soluble polymer diol, whereby a diisocyanate is used as chain-extender and the water-soluble polymer content is held constant or is decreased. The water-soluble polymer in the third segment is built in the multi-block copolymer with a slowly degrading urethane bond, compared to a faster degrading ester bond of the water-soluble polymer in pre-polymer (A).

Biologically active compounds which may be contained in the multi-block copolymer matrix, such as a poly(D,L-lactic acid)-co-PEG-co-poly(D,L-lactic acid)-b-PLLA ((PDLLA-co-PEG-co-PDLLA)-b-PLLA) matrix or a poly(ε-caprolactone)-co-PEG-co-poly(ε-caprolactone)-b-PLLA ((PCL-co-PEG-co-PCL)-b-PLLA) matrix, include but are not limited to non-peptide, non-protein small sized drugs having a molecular weight which in general is 1000 Da or less and biologically active polypeptides.

Examples of non-peptide, non-protein small sized drugs which may be contained in the polyetherester urethane matrix such as a (PDLLA-co-PEG-co-PDLLA)-b-PLLA matrix or a PCL-co-PEG-co-PCL)-b-PLLA matrix, include but are not limited to anti-tumour agents, anti-microbial agents, including antibiotics, cephalosporins, aminoglycosides; macrolides; tetracyclines, chemotherapeutic agents including sulphonamides; urinary tract antiseptics; drugs for anaerobic infections; drugs for tuberculosis; drugs for leprosy, antifungal agents, antiviral agents, anti-helminthiasis agents, anti-inflammatory, anti-gout agents, centrally acting (opoid) analgesics, local anaesthetics, drugs for Parkinson Disease, centrally acting muscle relaxants, hormones and hormone antagonists, corticosteroids, glucocorticosteroids, androgens, androgenic steroids, anabolic steroids, antiandrogens, estrogens, estrogenic steroids, anti-estrogens, progestins; thyroid drugs and anti-thyroid drugs.

When a small-sized drug, such as those hereinabove described, is contained in a (PDLLA-co-PEG-co-PDLLA)-b-PLLA matrix, the PEG component of the copolymer preferably has a molecular weight of from 200 to 1500 g/mol, preferably from 600 to 1000 g/mol, and is present in the copolymer in an amount of from 5 wt. % to 20 wt. % of the weight of the copolymer, preferably in an amount of from 5 wt. % to 10 wt. % of the weight of the copolymer. In general, the PLLA is present in the copolymer in an amount of from 20 wt. % to 90 wt. % of the weight of the copolymer, preferably in an amount of from 30 wt. % to 70 wt. % of the copolymer. The at least one small-sized drug molecule may be present in the matrix in an amount of from 0.1 wt. % to 80 wt. %, preferably from 1.0 wt. % to 40 wt. %, most preferably from 5 to 20 wt. %. If it is desired to increase the hydrophilicity of the multi-block copolymer, and thereby increase the degradation rate of the copolymer and the release rate of the incorporated biologically active compound, the copolymer may be modified by replacing partially or completely the D,L-lactide of the hydrophilic segment by glycolide and/or by using a PEG component with a higher molecular weight or by increasing the weight fraction of PEG component in the pre-polymer segment. If it is desired to decrease the hydrophilicity of the polymer, and thereby decrease the degradation rate of the copolymer, and the release rate of the incorporated biologically active compound, the copolymer may be modified by replacing partially or completely the D,L-lactide of the hydrophilic segment by ε-caprolactone and/or by using a PEG component with a lower molecular weight or by decreasing the weight fraction of PEG component in the pre-polymer segment.

A polypeptide consists of amino acids linked by peptide bonds. Short polypeptides are also referred to as peptides, whereas longer polypeptides are typically referred to as proteins. One convention is that those polypeptide chains that are short enough to be made synthetically from the constituent amino acids are called peptides rather than proteins. However, with the advent of better synthetic techniques, polypeptides as long as hundreds of amino acids can be made, including full proteins like ubiquitin. Another convention places an informal dividing line at approximately 50 amino acids in length. This definition is somewhat arbitrary. Long polypeptides, such as the amyloid beta peptide linked to Alzheimer's disease, can be considered proteins; and small proteins, such as insulin, can be considered peptides. At any rate, the skilled person will appreciate that essentially any type of polypeptide can be encapsulated and subsequently released from a copolymer matrix.

In one embodiment, a composition of the invention comprises a biologically active peptide or biologically active protein. Encapsulated polypeptides preferably contain only natural amino acids, although non-natural amino acids (i.e. compounds that do not occur in nature but that can be incorporated into a polypeptide chain) and/or amino acid analogues as are known in the art may alternatively be employed. Also, one or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalisation, or other modification (e.g. alpha amidation), etc.

In a preferred embodiment, the modifications of the peptide lead to a more stable peptide (e.g. greater half-life in vivo). These modifications may include cyclisation of the peptide, the incorporation of D-amino acids, etc. None of the modifications should substantially interfere with the desired biological activity of the peptide. In certain embodiments, the modifications of the peptide lead to a more biologically active peptide.

The biologically active polypeptide is preferably selected from the group consisting of protein/peptide drugs, enzymes, receptor ligands, neurotransmitters, inhibitory peptides, regulatory peptides, activator peptides, cytokines, growth factors, monoclonal antibodies, monoclonal antibodies fragments, anti-tumour peptides, antibiotics, antigens, vaccines and hormones. Exemplary polypeptides to be encapsulated are mentioned in U.S. Pat. No. 5,980,948 and Crommelin et al., *Int. J. Pharm.* 2003, 266(1-2), 3-16. Of course, it is also envisaged to encapsulate two or more distinct (biologically active) polypeptides.

The size of the polypeptide(s) can vary. In one embodiment, the polypeptide has a molecular weight of 10 000 Da or less. It was found that polypeptides of such size are particularly suitable to be encapsulated in the matrix of a copolymer comprising PEG as a segment of pre-polymer (A) and/or as an additional pre-polymer, said PEG having a number average molecular weight of from 400 to 3000 g/mol, preferably from 600 to 1500 g/mol. Alternatively, or in addition, said PEG is present in an amount of from 5 wt. % to 60 wt. % based on total weight of the copolymer, preferably of from 5 wt. % to 40 wt. %.

In another embodiment, said polypeptide is a biologically active protein having a molecular weight of 10 000 Da or more. These larger polypeptides are preferably encapsulated in the matrix of a copolymer which contains PEG, as a segment of pre-polymer (A) and/or as an additional pre-polymer, and wherein said PEG has a number average molecular weight of from 600 to 5000 g/mol, preferably from 1000 to 3000 g/mol and/or wherein said PEG is present in an amount of from 5 wt. % to 70 wt. % based on total weight of the copolymer, more preferably of from 10 wt. % to 50 wt. %.

A composition of the invention can have any desirable appearance or shape. In one embodiment, multi-block copolymers of the current invention are processed in the form of microspheres, microparticles, sprays, an implant, a coating, a gel, a film, foil, sheet, membrane or rod.

One specific aspect relates to a composition in the form of microspheres. In general microspheres are fine spherical particles having a diameter of less than 1000 μm, and containing a biologically active compound. The microsphere may be a homogeneous or monolithic microsphere in which the biologically active compound is dissolved or dispersed throughout the polymer matrix. It is also possible that the microsphere is of a reservoir type in which the biologically active compound is surrounded by a polymer in the mononuclear or polynuclear state. When the biologically active compound is a small sized water-soluble drug, the drug may first be dispersed in a hydrophobic or lipophilic excipient, which combination then is dispersed in the form of particles, droplets, or microsuspensions in the polymer matrix. Microspheres can then be formed from the emulsion.

The microspheres may be prepared by techniques known to those skilled in the art, including but not limited to coacervation, solvent extraction/evaporation, spray drying or spray-freeze drying techniques.

In one embodiment, the microspheres are prepared by a solvent extraction/evaporation technique which comprises dissolving the multi-block copolymer in an organic solvent such as dichloromethane, and emulsification of the multi-block copolymer solution in an aqueous phase containing an emulsifying agent, such as polyvinyl alcohol (as described among others by Okada, *Adv. Drug Del. Rev.* 1997, 28(1), 43-70).

The characteristics, such as particle size, porosity and drug loading of the so-formed microspheres depend on the process parameters, such as viscosity or concentration of the aqueous polyvinyl alcohol phase, concentration of the multi-block copolymer solution, ratio of dichloromethane to aqueous solution of active, ratio of primary emulsion to polyvinyl alcohol phase and the stirring rate.

When the microspheres are formed by a spray-drying process, a low concentration of multi-block copolymer from 0.5 wt. % to 5 wt. %, preferably about 2 wt. %, in the organic solvent, such as dichloromethane, is employed. Spray-drying results in general in the formation of porous, irregularly shaped particles.

As the microspheres are being formed, a biologically active compound is encapsulated in the microspheres or microparticles. In general, when the solvent extraction/evaporation technique is employed to encapsulate lipophilic compounds, the compound is first dissolved in the solution of the multi-block copolymer in an organic solvent such as dichloromethane or ethyl acetate. The organic solution is then subsequently emulsified in an aqueous polyvinyl alcohol solution, which yields an oil-in-water (O/W) emulsion. The organic solvent is then extracted into the aqueous phase and evaporated to solidify the microspheres.

In general, when the solvent evaporation technique is employed to encapsulate water-soluble compound, an aqueous solution of the compound is first emulsified in a solution of the multi-block copolymer in an organic solvent such as dichloromethane. This primary emulsion is then subsequently emulsified in an aqueous polyvinyl alcohol solution, which yields a water-in-oil-in-water (W/O/W) emulsion. The organic solvent, such as dichloromethane or ethyl acetate, is then extracted similarly to the 0/W process route to solidify the microspheres. Alternatively, water-soluble agents may be dispersed directly in a solution of the multi-block copolymer in an organic solvent. The obtained dispersion is then subsequently emulsified in an aqueous solution comprising a surfactant such as polyvinyl alcohol, which yields a solid-in-oil-in-water (S/O/W) emulsion. The organic solvent is then extracted similarly to the O/W process route to solidify the microspheres.

When W/O/W and S/O/W emulsification routes are used to encapsulate water-soluble compound, it may be challenging to obtain microspheres with sufficient encapsulation efficiency. Due to the water-soluble character of the compound, part of the compound may be lost to the aqueous extraction medium such as aqueous polyvinyl alcohol solution. A viscosifier, such as gelatin, may be used in the internal water phase, to decrease diffusion of the compound in the internal water phase to the external water phase. Also, additives may be added to the external water phase to decrease the solubility of the compound in the external water phase. For this purpose, salts may be used or the pH may be adjusted.

Water-in-oil-in-oil (W/O/O) or solid-in-oil-in-oil (S/O/O) emulsification routes provide an interesting alternative to obtain microspheres with sufficient encapsulation efficiency. In the W/O/O process the biologically active compound is, similar to a W/O/W process, dissolved in an aqueous solution and emulsified with a solution of the polymer in an organic solvent, such as typically dichloromethaneor ethyl acetate. Subsequently, a polymer precipitant, such as silicon oil, is then slowly added under stirring to form embryonic microparticles, which are then poured into heptane or hexane to extract the silicone oil and organic solvent and solidify the microspheres. The microparticles may be collected by vacuum filtration, rinsed with additional solvent and dried under vacuum. In the S/O/O emulsification route the biologically active compound is, similar to a S/O/W process, dispersed as a solid powder in a solution of the polymer in an organic solvent, such as dichloromethane or ethyl acetate. Subsequently, a polymer precipitant, such as silicon oil, is then slowly added under stirring to form embryonic microparticles, which are then poured into heptane or hexane to extract the silicone oil and dichloromethane and solidify the microspheres.

Stabilising agents may be added to the aqueous solution of protein to prevent loss of protein activity during processing into microspheres. Examples of such stabilisng agents are human serum albumin, gelatin and carbohydrates, such as trehalose, inulin and sucrose.

When the spray-drying technique is employed, an aqueous solution of the compound is emulsified in a solution of the copolymer in an organic solvent such as methylene chloride, as hereinabove described. The water-in-oil emulsion is then spray-dried using a spray dryer.

In further embodiments, the composition of the invention is in the form of a coating, an injectable gel, an implant (preferably an injectable implant) or a coated implant. The composition in the form of a coating may be applied as a drug-eluting coating e.g. on a medical implant, such as a vascular or urinary stent, an orthopaedic prosthesis or an ocular implant.

Biologically active compounds may be formulated into injectable solid implants via extrusion. Typically, the compound and multi-block copolymer powders are physically mixed where after the resulting powder blend is introduced to the extruder, heated and processed to yield formulations of the desired shape and dimensions, such as a small diameter cylindrical rod. Instead of physical mixing of the compound and multi-block copolymer powders, the compound and polymer may be co-dissolved in a suitable solvent or a dispersion of compound in a solution of polymer in a suitable solvent may be prepared, followed by freeze-drying and extrusion of the freeze-dried powder. The latter generally improves the blend homogeneity and the content uniformity of the implants.

In yet another aspect the invention is directed to a method of delivering a biologically active compound to a subject in need thereof, comprising administering an effective dose of a composition as defined herein to said subject.

The subject is typically a mammal, preferably a human. However, veterinary use of the invention is also encompassed. The method can have a therapeutic, prophylactic, and/or cosmetic purpose. Any suitable mode of administration can be selected, depending on the circumstances. For example, administering may comprise the parenteral, oral, intra-arterial, intra-articular, intra-venal, intra-ocular, epidural, intra-thecal, intra-muscular, intra-peritoneal, intravenous, intra-vaginal, rectal, topical or subcutaneous administration of the composition. In one embodiment, the invention provides a method for delivering a biologically active polypeptide of interest to a subject in need thereof, comprising administering an effective dose of a composition according to the invention to said subject, wherein the composition is in the form of microspheres, an injectable implant or an in situ forming gel and wherein the composition is administered intra-ocularly, intra-arterially, intra-muscularly or subcutaneously.

For topical administration, the microspheres may be contained in a gel, cream, or ointment, and may, if desired, be covered by a barrier. Thus, the microspheres may contain one or more biologically active compounds employed in the treatment of skin diseases, such as psoriasis, eczema, seborrhoea, and dermatitis.

In another embodiment, the microspheres may be contained in a gel such as a hyaluronic acid gel or a macromolecular polysaccharide gel. Such an embodiment is applicable particularly to parenteral applications, such as during and after surgery.

When administered via injection, the microspheres may be contained in a pharmaceutical carrier such as water, saline solution (for example, 0.9%), or a solution containing a surfactant in an amount of from 0.1% w/v to 0.5% w/v. Examples of surfactants which may be employed include, but are not limited to, Tween 80 surfactant. The pharmaceutical carrier may further contain a viscosifier, such as sodium carboxymethylcellulose.

When administered via injection, the microspheres have an average size of from 1 μm to 200 μm, preferably from 5 μm to 100 μm, most preferably from 10 μm to 50 μm. Such microspheres, when administered in combination with an acceptable pharmaceutical carrier, may be employed in the treatment of a variety of diseases or disorders, depending upon the biologically active compound that is encapsulated. Thus, injectable formulations including the microspheres of the invention may be employed in the treatment of systemic diseases such as rheumatoid arthritis, hepatitis, diabetes, or metabolic syndromes, and locally confined diseases such as osteoarthritis, renal diseases, inflammations, local pain processes, local infections, local skin diseases, tumours (or their sites after surgical removal as a postoperative treatment to destroy any tumour cells possibly remaining), prostate or breast cancer, agromegaly, ocular diseases such as age-related macular degeneration, local brain diseases (e.g. Parkinson's disease), and cardiovascular diseases such as acute myocardial infarction, chronic heart failure or arthrosclerosis. Such injectable formulations also may be employed in long-term therapeutic treatments such as for example, treatments with corticosteroids, androgens, antiandrogens, estrogens, anti-estrogens, progestangenic agents, or thyroid hormones, or with anti-tuberculosis, anti-leprosy, or anti-malaria drugs.

BRIEF DESCRIPTION OF THE DRAWINGS

FIG. 12: SEM photo of 3-4 wt. % Protein A loaded microspheres composed of 30CP10C20-LL40 (IV 0.71 dl/g) prepared using various amounts of inulin in the inner aqueous phase A: 0% inulin, B: 2% inulin. 1: Overview. 2: Zoom-in.

EXAMPLES

Figure 1A:
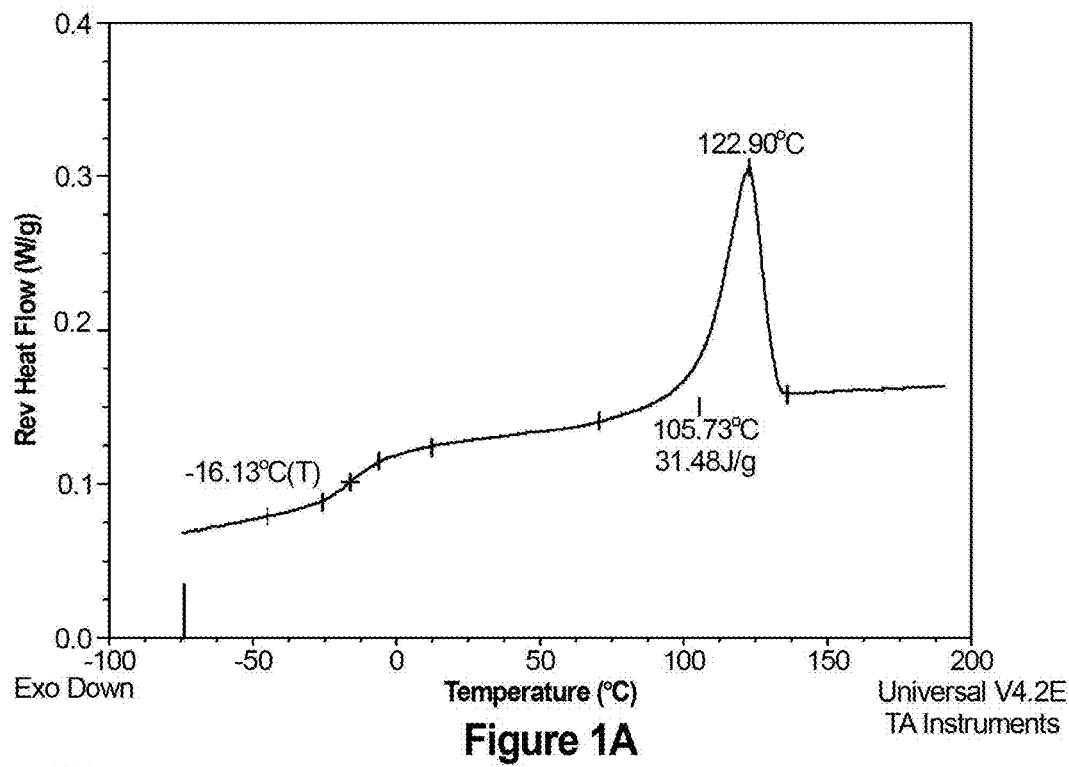
FIG. 1A: DSC thermograms of 50LP10L20-LL40

In the following examples various biodegradable semi-crystalline, phase separated multi-block copolymers were synthesised and evaluated for their processing and controlled release characteristics. The polymers were composed of a crystalline L-lactide-based hard segment B with a melting point ($T_m$) and a hydrophilic poly(ethylene glycol) (PEG)-based segment A having a glass transition temperature ($T_g$) that was below body temperature under physiological conditions. In the following examples PEG is denoted with its molecular weight (MW). For example $PEG_{1000}$ refers to PEG with MW 1000 g/mol.

Example 1

In this example, general procedures for the preparation of poly(DL-lactide-co-PEG) prepolmer (A) are provided. Monomers were weighed into a three-necked bottle under nitrogen atmosphere and dried at 50° C. in case of glycolide and D,L-lactide for at least 16 h under reduced pressure. PEG was dried at 90° C. under reduced pressure for at least 16 h. PEG was added to the monomer(s) under nitrogen atmosphere. Subsequently, stannous octoate was added and the mixture was magnetically stirred and reacted at 140° C. for several days. $^1$H-NMR was performed on a VXR Unity Plus NMR Machine (Varian) operating at 300 MHz. The $d_1$ waiting time was set to 20 s, and the number of scans was 16. Spectra were recorded from 0 to 14 ppm. Conversion and pre-polymer $M_n$ was determined from $^1$H-NMR. $^1$H-NMR samples were prepared by dissolving 10 mg of polymer into 1 ml of deuterated chloroform.

Example 2

This example describes the preparation of poly(DL-lactide-co-$PEG_{1000}$) (pLP10L20) with $M_n$ 2000 g/mol. 149.84 grams (1.04 mol) of D,L-lactide (Purac) was weighed and 149.21 g (0.149 mol) of PEG MW1000 (Ineos, PU grade) was added. 71.6 mg of stannous octoate (Sigma Corp) was added (monomer/catalyst molar ratio=5900) and the mixture was magnetically stirred and reacted at 140° C. during 245 h. $^1$H-NMR showed 94.8% monomer conversion. The calculated molecular weight ($M_n$) from in-weights was 2000 g/mol. Molecular weight as determined by $^1$H-NMR was 1950 g/mol.

Example 3

This example describes the preparation of poly(DL-lactide-co-$PEG_{3000}$) (pLP30L40) with $M_n$ 4000 g/mol. 50.35 g (0.349 mol) of D,L-lactide (Purac) was weighed and 151.08 g (50.4 mmol) of PEG MW3000 (Sigma Corp) was added. 37.5 mg of stannous octoate (Sigma Corp) was added (monomer/catalyst molar ratio=4300) and the mixture was magnetically stirred and reacted at 140° C. during 90 h. $^1$H-NMR showed 93.4% monomer conversion. The calculated molecular weight ($M_n$) from in-weights was 4000 g/mol. Molecular weight as determined by $^1$H-NMR was 3940 g/mol.

Example 4

This example describes the preparation of poly(ε-caprolactone-co-$PEG_{1000}$) pre-polymer (pCP10C20) with $M_n$ 2000 g/mol. 100.81 g (0.101 mol) of PEG MW1000 (Ineos, PU grade) was weighed into a three-necked bottle under nitrogen atmosphere and dried at 90° C. for at least 16 h under reduced pressure. 101.76 g (0.892 mol) of ε-caprolactone (Acros, previously dried and distilled over $CaH_2$ under reduced pressure) was added to the PEG under nitrogen atmosphere and the mixture was heated to 135° C. 57.9 mg of stannous octoate (Sigma Corp) was added (monomer/catalyst molar ratio=6200) and the mixture was magnetically stirred and reacted at 135° C. during 76 h. $^1$H-NMR showed 100% monomer conversion. The calculated molecular weight ($M_n$) from in-weights was 2010 g/mol. Molecular weight as determined by $^1$H-NMR was 1950 g/mol.

Example 5

This example describes the preparation of poly(ε-caprolactone-co-$PEG_{3000}$) pre-polymer (pCP30C40) with $M_n$ 4000 g/mol. 176.60 g (58.9 mmol) of PEG MW3000 (Ineos, PU grade) was weighed into a three-necked bottle under nitrogen atmosphere and dried at 90° C. for at least 16 h under reduced pressure. 59.4 g (0.520 mol) of ε-caprolactone (Acros, previously dried and distilled over $CaH_2$ under reduced pressure) was added to the PEG under nitrogen atmosphere and the mixture was heated to 135° C. 69.6 mg of stannous octoate (Sigma Corp) was added (monomer/catalyst molar ratio=3000) and the mixture was magnetically stirred and reacted at 135° C. during 243 h. $^1$H-NMR showed 100% monomer conversion. The calculated molecular weight ($M_n$) from in-weights was 2010 g/mol. Molecular weight as determined by $^1$H-NMR was 1950 g/mol.

Example 6

This example describes the preparation of poly(L-lactic acid) pre-polymer (LL4000) with $M_n$=4000 g/mol initiated by 1,4-butanediol (BDO). 399.89 g (2.77 mol) of L-lactide (Purac) was weighed into a three-necked bottle under nitrogen atmosphere and dried at 50° C. for at least 16 h under reduced pressure. 9.36 g (0.104 mol) of BDO (Acros, previously distilled under reduced pressure) was added to the L-lactide under nitrogen atmosphere. 434 ml of dioxane (Acros, previously dried and distilled over sodium wire) was added to dissolve the L-lactide and BDO and the mixture was heated to 80° C. 87.8 mg of stannous octoate (Sigma Corp) was added (monomer/catalyst molar ratio=12 800). The mixture was magnetically stirred and reacted at 80° C. during 50.6 h. The polymer was retrieved from dioxane by freeze-drying for 72 h to a final temperature of 50° C. In case of polymer dissolved in dioxane, the dioxane was first removed under reduced pressure at 50° C. $^1$H-NMR showed 96.5% monomer conversion. The calculated molecular weight ($M_n$) from in-weights was 3940 g/mol. Molecular weight as determined by $^1$H-NMR was 3900 g/mol. After freeze-drying dioxane content was determined by $^1$H-NMR (300 MHZ, 50 mg of polymer dissolved into 1 ml of deuterated chloroform, $d_1$=30 s, 32 scans). 5 mg of dibromobenzene (Acros) was dissolved in the sample for quantification of the dioxane. Dioxane content was found to be 1193 ppm.

Example 7

This example describes the general procedures used for the preparation of multi-block copolymers. ε-Caprolactone-co-PEG-co-ε-caprolactone (CPC) or D,L-lactide-co-PEG-co-D,L-lactide pre-polymers (LPL) ($M_n$ 2000 g/mol) were heated to 50-80° C. until they became more liquid. The appropriate amounts of LL4000 pre-polymer ($M_n$ 4000 g/mol) and CPC or LPL pre-polymer were weighted into a glass ampoule supplied with nitrogen inlet and dried at 50° C. for at least 48 h. Subsequently, the glass ampoule was supplied with a mechanical stirrer. 1,4-Dioxane (Acros, distilled over sodium) was added to a polymer concentration of 30 wt. % and the contents of the ampoule were heated to 80° C. to dissolve the pre-polymers. 0.900-0.990 equivalent (with respect to the pre-polymer hydroxyl groups) of 1,4-butanediisocyanate (Bayer, distilled at reduced pressure) was added and the reaction mixture was stirred mechanically for 16-22 h. Non-distilled dioxane was added to a polymer concentration of 20 wt. % to quench unreacted isocyanate groups. The reaction mixture was further diluted with non-distilled dioxane to a polymer concentration of 10 wt. %. The ampoule was cooled to room temperature, the reaction mixture was poured into a tray and frozen at −18° C. Subsequently, dioxane was removed by placing the frozen reaction mixture under vacuum at 30° C. The polymer was stored in a sealed package at −18° C. A small part of the batch was analysed for thermal properties (mDSC), dioxane content (gas chromatography), intrinsic viscosity and polymer composition ($^1$H-NMR). Thermal analysis was performed by Modulated Differential Scanning calorimetry (mDSC). Samples of 5-10 mg were weighed in a DSC pan. The measurement was performed on a DSC Q1000 (TA Instruments) using a modulated temperature program. Amplitude was set to 1° C., the modulation period to 60 s and the heating rate to 5° C./min. Samples were heated from −80° C. to 100-200° C. (depending on the type of polymer). Intrinsic viscosity was measured using an Ubbelohde Viscosimeter (DIN), type 0C, 0a or I, Schott Geräte supplied with a Schott AVS-450 Viscosimeter including a water bath. The measurements were performed in chloroform at room temperature. The polymer concentration in chloroform was such that the relative viscosity was in the range of 1.2 to 2.0. Dioxane content was determined using a GC-FID headspace method. Measurements were performed on a GC-FID Combi Sampler supplied with an Agilent Column, DB-624/30 m/0.53 mm. Samples were prepared in DMSO. Dioxane content was determined using dioxane calibration standards.

Example 8

This example describes the preparation of 20(D,L-Lactide-co-$PEG_{1000}$-co-D,L-lactide)$_{2000}$-80(L-lactide)$_{4000}$ (20LP10-L20-LL40). 42.02 g of LL40 pre-polymer ($M_n$ 4040 g/mol, 10.40 mmol) and 10.16 g of D,L-lactide-co-$PEG_{1000}$-D,L-lactide pre-polymer ($M_n$ 2000 g/mol, 5.08 mmol) were weighed and dissolved in 100 ml of 1,4-dioxane at 80° C. 1.8466 g (13.2 mmol) of 1,4-butanediisocyanate was added (0.851 equivalent with respect to the pre-polymer hydroxyl groups) with 20 ml of 1,4-dioxane After 17 h the reaction was quenched with 88 ml of non-distilled dioxane and further diluted with 255 ml of non-distilled dioxane. The dioxane was removed by placing the frozen reaction mixture under vacuum at 30° C.

Example 9

This example describes the preparation of 30(D,L-lactide-co-$PEG_{1000}$-co-D,L-lactide)$_{2000}$-70(L-lactide)$_{4000}$ (30LP10-L20-LL40). 34.44 g of LL40 pre-polymer ($M_n$ 4020 g/mol, 8.57 mmol) and 14.95 g of D,L-lactide-co-$PEG_{1000}$-D,L-lactide pre-polymer ($M_n$ 2040 g/mol, 7.33 mmol) were weighed and dissolved in 100 ml of 1,4-dioxane at 80° C. 2.7386 g (19.5 mmol) of 1,4-butanediisocyanate was added (1.231 equivalent with respect to the pre-polymer hydroxyl groups) with 20 ml of 1,4-dioxane After 20 h the reaction was quenched with 85 ml of non-distilled dioxane and further diluted with 240 ml of non-distilled dioxane. The dioxane was removed by placing the frozen reaction mixture under vacuum at 30° C.

Example 10

This example describes the preparation of 50(D,L-lactide-co-PEG$_{1000}$-co-D,L-lactide)$_{2000}$-50(L-lactide)$_{4000}$ (50LP10-L 20-LL40). 19.59 g of LL40 pre-polymer (M$_n$ 4060 g/mol, 4.83 mmol) and 19.57 g of D,L-lactide-co-PEG$_{1000}$-D,L-lactide pre-polymer (M$_n$ 2040 g/mol, 9.59 mmol) were weighed and dissolved in 78 ml of 1,4-dioxane at 80° C. 2.0018 g (14.3 mmol) of 1,4-butanediisocyanate was added (0.991 equivalent with respect to the pre-polymer hydroxyl groups) in 20 ml of 1,4-dioxane. After 20 h the reaction was quenched with 67 ml of non-distilled dioxane and further diluted with 189 ml of non-distilled dioxane. Dioxane was removed by placing the frozen reaction mixture under vacuum at 30° C.

Example 11

This example describes the preparation of 70(D,L-lactide-co-PEG$_{1000}$-co-D,L-lactide)$_{2000}$-30(L-lactide)$_{4000}$ (70LP10-L20-LL40). 8.59 g of LL40 pre-polymer (M$_n$ 4020 g/mol, 2.14 mmol) and 19.96 g of D,L-lactide-co-PEG$_{1000}$-D,L-lactide pre-polymer (M$_n$ 2040 g/mol, 9.78 mmol) were weighed and dissolved in 48 ml of 1,4-dioxane at 80° C. 1.648 g (11.8 mmol) of 1,4-butanediisocyanate was added (0.986 equivalent with respect to the pre-polymer hydroxyl groups) with 20 ml of 1,4-dioxane After 21 h the reaction was quenched with 49 ml of non-distilled dioxane, and further diluted with 147 ml of non-distilled dioxane. The dioxane was removed by placing the frozen reaction mixture under vacuum at 30° C.

Example 12

This example describes the preparation of 30(D,L-lactide-co-PEG$_{3000}$-co-D,L-lactide)$_{4000}$-70(L-lactide)$_{4000}$ (30LP30L-40-LL40). 29.96 g of LL40 pre-polymer (M$_n$ 4030 g/mol, 7.43 mmol) and 14.01 g of D,L-lactide-co-PEG$_{1000}$-D,L-lactide pre-polymer (M$_n$ 4000 g/mol, 3.50 mmol) were weighed and dissolved in 83 ml of 1,4-dioxane at 80° C. 1.52 g (10.8 mmol) of 1,4-butanediisocyanate was added (0.992 equivalent with respect to the pre-polymer hydroxyl groups) with 20 ml of 1,4-dioxane. After 21 h the reaction was quenched with 74 ml of non-distilled dioxane and further diluted with 222 ml of non-distilled dioxane. The dioxane was removed by placing the frozen reaction mixture under vacuum at 30° C.

Example 13

This example describes preparation of 50(ε-caprolactone-co-PEG$_{1000}$-co-ε-caprolactone)$_{2000}$-50(L-lactide)$_{4000}$ (50CP10C20-LL40). 24.34 g of LL40 pre-polymer (M$_n$ 4030 g/mol, 6.04 mmol) and 23.87 g of ε-caprolactone-co-PEG$_{1000}$-ε-caprolactone pre-polymer (M$_n$ 2010 g/mol, 11.9 mmol) were weighed and dissolved in 95 ml of 1,4-dioxane at 80° C. 2.4098 g (17.2 mmol) of 1,4-butanediisocyanate was added (0.960 equivalent with respect to the pre-polymer hydroxyl groups) with 20 ml of 1,4-dioxane. After 18 h the reaction was quenched with 82 ml of non-distilled dioxane and further diluted with 246 ml of non-distilled dioxane. The dioxane was removed by placing the frozen reaction mixture under vacuum at 30° C.

Example 14

This example describes preparation of 30(ε-caprolactone-co-PEG$_{3000}$-co-ε-caprolactone)$_{4000}$-70(L-lactide)$_{4000}$ (30C-P30C40-LL40). 35.84 g of LL40 pre-polymer (M$_n$ 4030 g/mol, 8.89 mmol) and 14.79 g of ε-caprolactone-co-PEG$_{3000}$-ε-caprolactone pre-polymer (M$_n$ 4010 g/mol, 3.69 mmol) were weighed and dissolved in 100 ml of 1,4-dioxane at 80° C. 1.7428 g (12.4 mmol) of 1,4-butanediisocyanate was added (0.988 equivalent with respect to the pre-polymer hydroxyl groups) with 20 ml of 1,4-dioxane. After 18 h the reaction was quenched with 83 ml of non-distilled dioxane and further diluted with 240 ml of non-distilled dioxane. The dioxane was removed by placing the frozen reaction mixture under vacuum at 30° C.

Example 15

The synthesised multi-block copolymers were analysed for chemical composition, molecular weight and residual dioxane content. Table 1 shows the collected analysis results for 20LP10L20-LL40, 30LP10L20-LL40, 50LP10L20-LL40, 70LP10L20-LL40, 30LP30L40-LL40, 50CP10C20-LL40, 30CP30C40-LL40. The actual composition of the copolymers, as determined by $^1$H-NMR from L/P and C/P molar ratios resembled the target composition well. All polymers had an intrinsic viscosity between 0.7 and 1.1 dl/g. Dioxane contents were well below 1000 ppm indicating effective removal of dioxane by vacuum-drying.

Figure 1B:
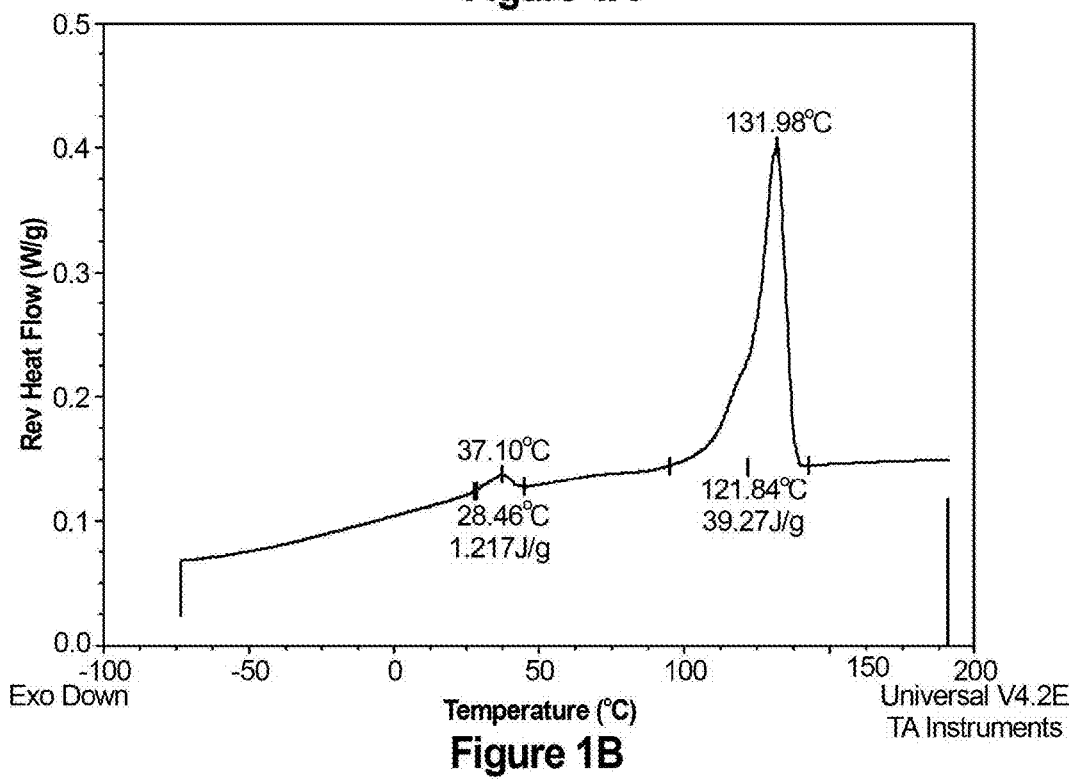
FIG. 1B: DSC thermograms of 30LP30L40-LL40
Figure 1C:
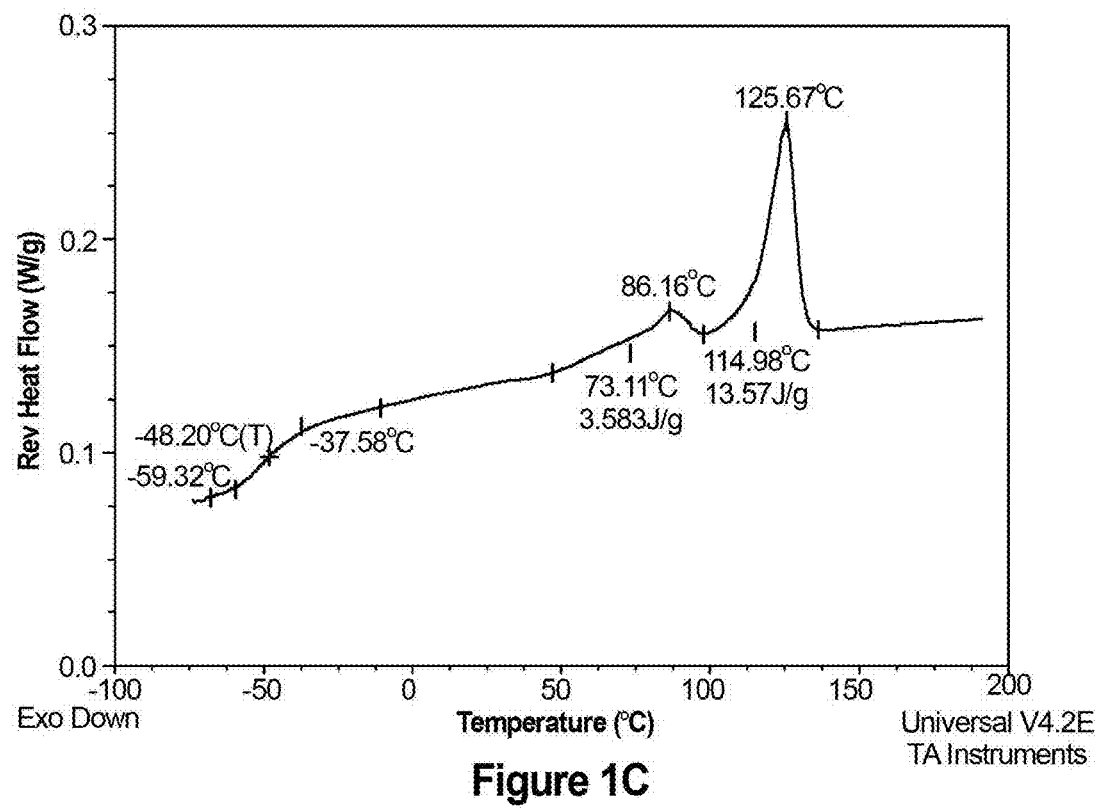
FIG. 1C: DSC thermograms of 50CP10C20-LL40

The multi-block copolymers were analysed for their thermal properties to confirm their phase separated morphology. Results are shown in Table 2. FIG. 1 shows typical DSC thermograms of 50LP10L20-LL40 (FIG. 1A), 30LP30L40-LL40 (FIG. 1B) and 50CP10C20-LL40 (FIG. 1C) multi-block copolymers. All multi-block copolymers exhibited a melting temperature (T$_m$) at approximately 120-133° C., due to melting of the LL40 segment. As expected, the melting enthalpy (ΔH$_m$) of the crystalline LLA40 segment increased with increasing amount of the segment. 70LP10L40-LL40, 50CP10C20-LL40 also exhibited a T$_m$ at approximately 85° C., which is attributed to melting of less perfect crystals of LL40. Copolymers containing PEG$_{3000}$ showed a T$_m$ at approximately 40° C., due to melting of the PEG. The glass transition temperature (T$_g$) of the multi-block copolymers is in general in between that of pre-polymer (A) and pre-polymer (B), indicating phase mixing of the amorphous pre-polymer (A) with the amorphous content of pre-polymer (B). The T$_g$ of LP10L20-LL40 type multi-block copolymers increased from −18 to 50° C. when increasing the LLA40 segment from 30 to 80 wt. %. The T$_g$ of these multi-block copolymers is in between that of pre-polymer (A) (pLP10L20, T$_g$−37° C.) and pre-polymer (B) (LL40, T$_g$~50° C.) and is thus attributed to mixing of amorphous polylactide of the semi-crystalline LL40 block and PEG. 50CP10C20-LL40 had a T$_g$ of −48° C., which is similarly attributed to mixing of amorphous PEG, polycaprolactone and polylactide. Table 3 shows the swelling degree of the multi-block copolymers. To measure the swelling characteristics of polymers, polymer films were made by pouring a 13 wt. % polymer solution in dichloromethane (approximately 300 mg of polymer with 1.5 ml of dichloromethane), on a glass plate and spreading the polymer solution with a casting knife or poured into a Teflon™ mould. The dichloromethane was left to evaporate slowly overnight and the residual dichloromethane was removed by vacuum drying at 20° C. Resulting films had a thickness of 100-200 μm. For the swelling tests, 15-40 mg of circular films with a diameter of approximately 25 mm were weighed and immersed in a flask containing 10 ml of phosphate buffer pH 7.4 (ISO-15814). The samples were stored in an oven at 37° C. At each sampling time point, samples were collected and excess buffer solution was removed from the surface where after the samples were weighed on a 4-decimal balance. All tests were performed in duplicate. The swelling degree was found to increase gradually with the content of PEG of the copolymers and with PEG MW at approximately constant PEG content.

TABLE 1

Collected results regarding the chemical composition, intrinsic viscosity and residual dioxane content of multi-block copolymers 20LP10L20-LL40, 30LP10L20-LL40, 50LP10L20-LL40, 70LP10L20-LL40, 30LP30L40-LL40, 50CP10C20-LL40, 30CP30C40-LL40.

|  | 20LP10L20-LL40 | 30LP10L20-LL40 | 50LP10L20-LL40 | 70LP10L20-LL40 | 30LP30L40-LL40 | 50CP10C20-LL40 | 30CP30C40-LL40 |
|---|---|---|---|---|---|---|---|
| Molar L/P ratio in-weights | 126.1 | 78.2 | 42.1 | 26.3 | 137.4 | 27.8 | 130.1 |
| Molar L/P ratio $^1$H-NMR | 128.5 | 75.9 | 42.6 | 25.7 | 129.9 | 26.8 | 131.8 |
| Molar C/P ratio in-weights | — | — | — | — | — | 8.8 | 7.8 |
| Molar C/P ratio $^1$H-NMR | — | — | — | — | — | 8.2 | 8.8 |
| Intrinsic viscosity (dl/g) | 0.73 | 0.85 | 0.89 | 0.70 | 0.79 | 1.05 | 0.69 |
| Dioxane content (ppm) | <200 | 256 | <200 | <200 | <200 | <200 | <200 |

TABLE 2

Thermal characteristics of multi-block copolymers (MBCP) 20LP10L20-LL40, 30LP10L20-LL40, 50LP10L20-LL40, 70LP10L20-LL40, 30LP30L40-LL40, 50CP10C20-LL40, 30CP30C40-LL40 and their pre-polymers (PP) A and B.

|  | 20LP10L20-LL40 | 30LP10L20-LL40 | 50LP10L20-LL40 | 70LP10L20-LL40 | 30LP30L40-LL40 | 50CP10C20-LL40 | 30CP30C40-LL40 |
|---|---|---|---|---|---|---|---|
| $T_g$ (° C.) MBCP | 50 | 5 | −15 | −18 | — | −48 | — |
| $T_m$ (° C.) MBCP | 134 | 126 | 123 | 85/120 | 37/132 | 87/126 | 43/133 |
| $\Delta H_m$ (J/g) MBCP | 50 | 39 | 31 | 2/4 | 1/40 | 4/13 | 35/25 |
| $T_g$ (° C.) PP A | −37 | −37 | −37 | −37 | −39 | −67 | −67 |
| $T_m$ (° C.) PP A | — | — | — | — | 35/42 | 43 | 43 |
| $\Delta H_m$ (J/g) PP A | — | — | — | — | 37 (both peaks) | 91 | 85 |
| $T_g$ (° C.) PP B | 43 | 46 | 48 | 46 | 57 | 57 | 57 |
| $T_m$ (° C.) PP B | 85/131 | 117/134 | 136 | 117/134 | 137 | 137 | 137 |
| $\Delta H_m$ (J/g) PP B | 24 (both peaks) | 28 (both peaks) | 32 | 28 (both peaks) | 57 | 57 | 57 |

TABLE 3

Composition and swelling of multi-block copolymers 20LP10L20-LL40, 30LP10L20-LL40, 50LP10L20-LL40, 70LP10L20-LL40, 30LP30L40-LL40, 50CP10C20-LL40, 30CP30C40-LL40.

|  | wt. % Segment A | wt. % Segment B | MW PEG | wt. % PEG | Swelling degree (—) |
|---|---|---|---|---|---|
| 20LP10L20-LL40 | 20 | 80 | 1000 | 10 | xx |
| 30LP10L20-LL40 | 30 | 70 | 1000 | 15 | 1.03 |
| 50LP10L20-LL40 | 50 | 50 | 1000 | 25 | 1.13 |
| 70LP10L20-LL40 | 70 | 30 | 1000 | 35 | 1.26 |
| 30LP30L40-LL40 | 30 | 70 | 3000 | 22.5 | 1.16 |
| 50CP10C20-LL40 | 50 | 50 | 1000 | 25 | 1.18 |
| 30CP30C40-LL40 | 30 | 70 | 3000 | 22.5 | 1.67 |

Example 16

In this example various hydrophilic phase separated multi-block copolymers described in the examples above were evaluated for their protein release characteristics using bovine serum albumin (BSA, 69 kDa) and lysozyme (14 kDa) as model proteins.

Protein-loaded films containing 10 wt. % protein were prepared by mixing of approximately 150 µl of 20 wt. % protein solution with 1.5 ml of dichloromethane containing 300 mg of polymer for 30 s with an Ultra turrax at 18 000 rpm. The emulsion was spread on a glass plate with a casting knife or poured into a Teflon™ mould. The dichloromethane was left to evaporate slowly overnight and the residual dichloromethane was removed by vacuum drying at 20° C. Resulting films had a thickness of 80-120 µm.

For the release tests, 20 mg of protein loaded film were weighed and immersed in vials containing 5 ml of phosphate buffer pH 7.4 and stored in an oven at 37° C. At each sampling point, 1 ml of release medium was sampled and replaced with 1 ml of fresh buffer. The protein content of the release samples was determined with a Bicinchoninic Acid (BCA) assay (Pierce) using an Easys Expert 96 well plate reader.

The biological activity of released lysozyme was measured by means of a bacteria lysis test. Lysozyme loaded films were prepared as described above. A 0.01 wt. % lysozyme solutions was prepared to serve as a control by weighing 2.1 mg of lysozyme and adding 20 ml of phosphate buffer. Lysozyme-loaded films were weighed and immersed in vials containing 5 ml of phosphate buffer pH 7.4. Vials containing lysozyme-loaded films as well as freshly prepared lysozyme solutions were stored in an oven at 37° C. At each sampling point, 1 ml of release medium was sampled and replaced with 1 ml of fresh buffer. The protein content of the release samples was determined by BCA as described above. The activity of (released) lysozyme was determined by following the change in turbidity at 450 nm for 3 min of a bacteria dispersion (*Micrococcus lysodeikticus*, Sigma, 0.21 mg/ml) to which 10 µl of sample was added. A UV-VIS spectrometer (Varian) was used for this purpose. Samples were diluted if necessary to obtain a lysozyme concentration of 5-100 µg/ml. The lysozyme activity of the samples was calculated by comparing the slope of the obtained curves (the slope relates to the lysozyme activity) with the slope of a curve obtained with a fresh lysozyme solution.

Figure 2:
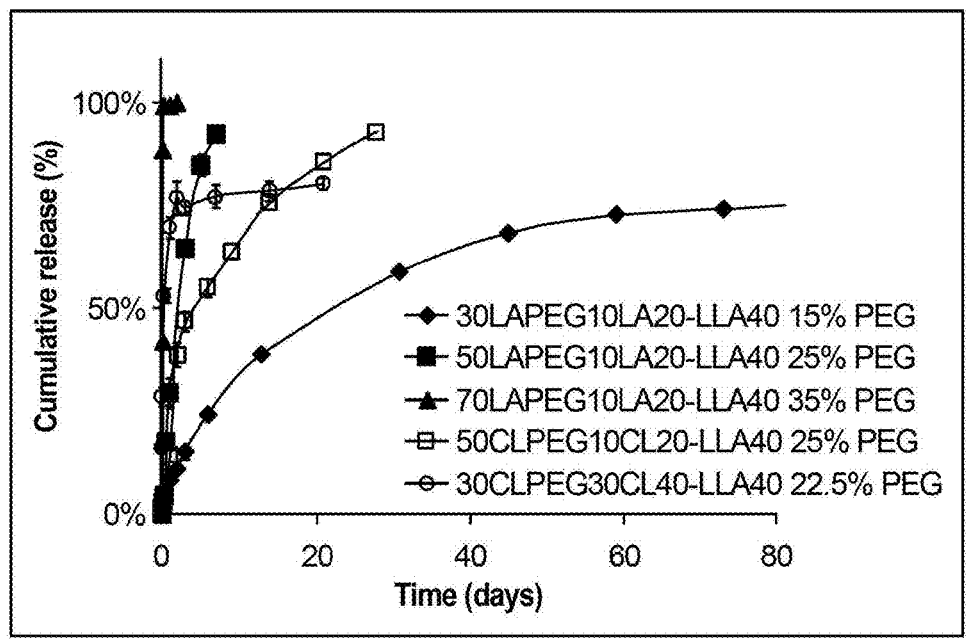
FIG. 2: Cumulative release of lysozyme from films composed of 30LP10L20-LL40, 50LP10L20-LL40, 70LP10L20-LL40, 50CP10C20-LL40 and 30CP30C40-LL40. Films were loaded with 10 wt. % lysozyme. Release was measured at 37° C. in phosphate buffer pH 7.4 (n=3).
Figure 3:
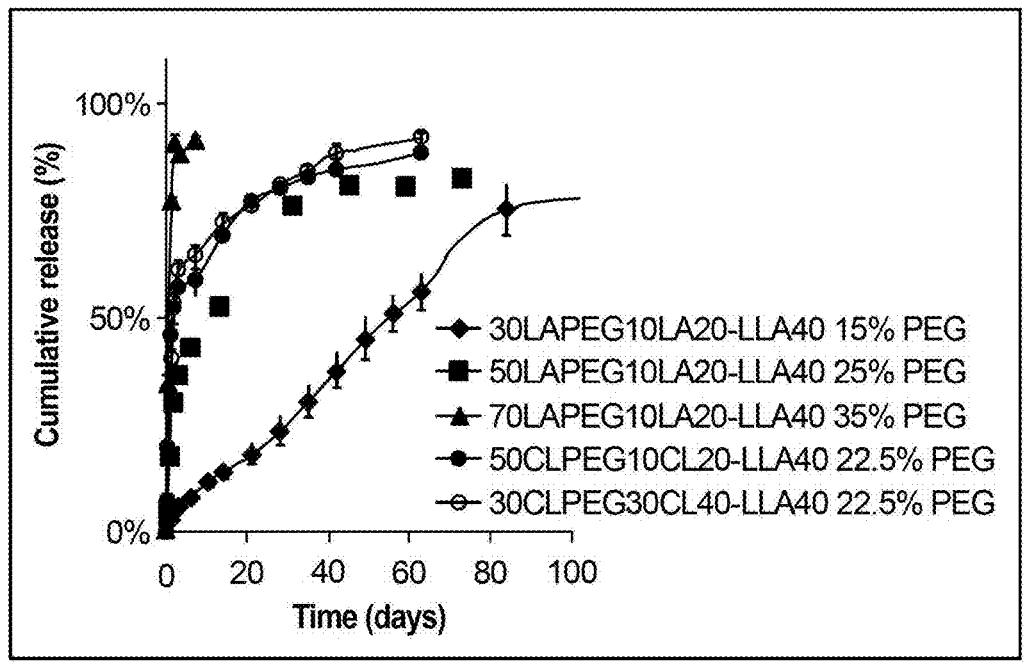
FIG. 3: Cumulative release of bovine serum albumin (BSA) from films composed of 30LP10L20-LL40, 50LP10L20-LL40, 70LP10L20-LL40, 30LP30L40-LL40 and 30CP30C40-LL40. Films were loaded with 10 wt. % BSA. Release was measured at 37° C. in phosphate buffer pH 7.4 (n=3).
Figure 4:
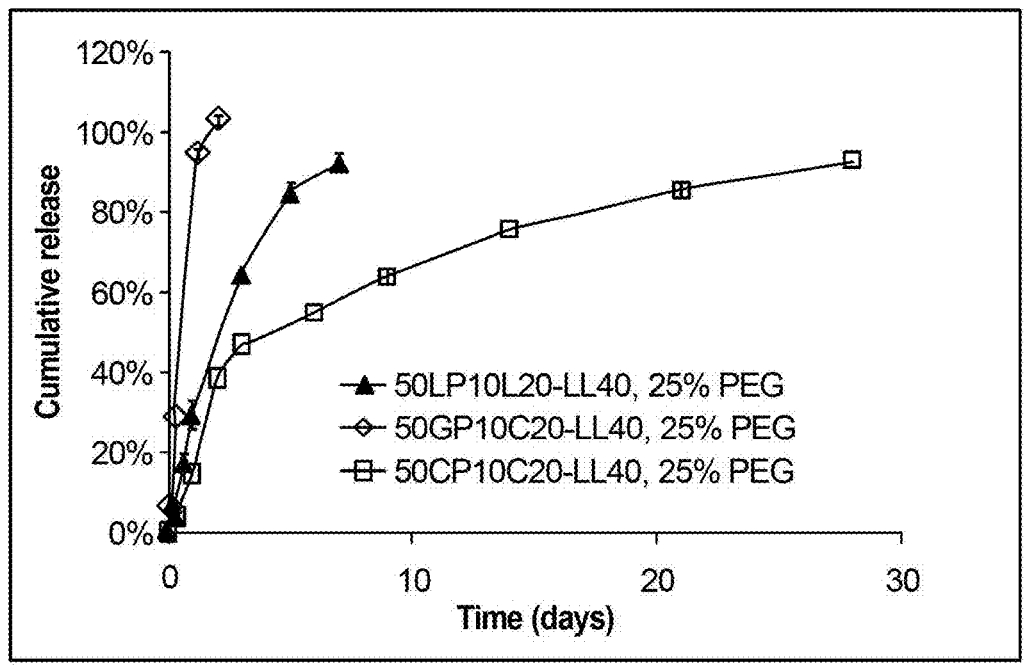
FIG. 4: Effect of composition of the hydrophilic block of multi-block copolymers on cumulative release of lysozyme from films. Films were composed of 50LP10L20-LL40, 50GP10C20-LL40 or 50CP10C20-LL40 (25 wt. % PEG1000) and were loaded with 10 wt. % lysozyme. Release was measured at 37° C. in phosphate buffer pH 7.4 (n=3).

FIGS. 2 and 3 show the release of respectively lysozyme and bovine serum albumin from the films. The results show that by changing the PEG content and PEG MW the release rate and profile can be varied. Lysozyme was released over periods varying from a few days up to approximately 3 months. Due to its larger size the release rate of BSA was lower resulting in release over periods ranging from a few days up to approximately 4 months. Furthermore, the release of lysozyme could be tuned by introducing different (combinations of) monomers adjacent to the PEG group in the hydrophilic block of the multi-block copolymers. The resulting multi-block copolymers (50LP10L20-LL40, 50GP10-C20-LL40 and 50CP10C20-LL40) contained 25 wt. % PEG1000 and exhibited similar swelling degrees, but different degradation rates leading to various release profiles for the encapsulated lysozyme. (FIG. 4).

Figure 5:
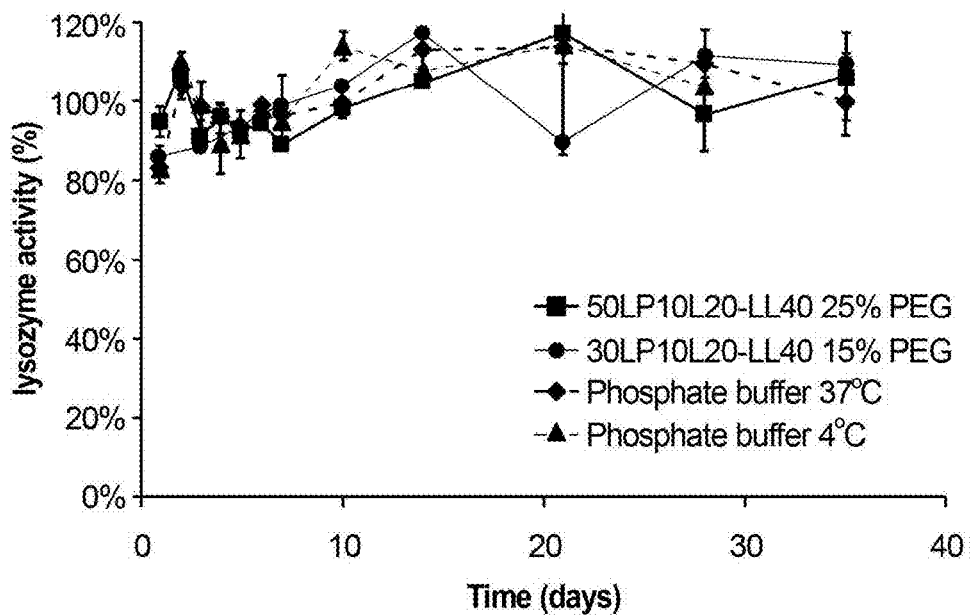
FIG. 5: Activity of lysozyme released from films composed of 30LP10L20-LL40 or 50LP10L20-LL40 containing 10 wt. % lysozyme (37° C., phosphate buffer pH 7.4) and lysozyme activity of lysozyme solutions (0.01 wt. %, phosphate buffer pH 7.4) stored at 4 and 37° C. as a function of time (n=3).

FIG. 5 shows the activity of lysozyme released from 10 wt. % lysozyme-loaded films of 30LP10L20-LL40 or 50LP10L20-LL40 (phosphate buffer pH 7.4, 37° C.). As a control the activity of lysozyme of the 0.01 wt. % lysozyme solutions 4 stored at 4 or 37° C. was measured (phosphate buffer pH 7.4). The results show that lysozyme released from the films over a period of approximately one month retained its biological activity, indicating that the structural integrity and biological activity of lysozyme was not only preserved during the encapsulation process but also during long-term presence of lysozyme in the hydrated and swollen polymer matrix at 37° C. prior to release.

Example 17

In this example 30LP10L20-LL40 (IV 0.85 dl/g) and 50CP10C20-LL40 (IV 1.06 dl/g) type phase separated copolymers were used to formulate BSA into microspheres.

BSA loaded microspheres were prepared of 50CP10C20-LL40 (IV 1.06 dl/g) and 30LP10L20-LL40 (IV 0.85 dl/g) hydrophilic phase separated multi-block copolymers by a solvent evaporation method using procedures as disclosed by by Kissel et al., *J. Contr. Rel.* 1996, 39(2), 315-326 and Meinel et al., *J. Contr. Rel.* 2001, 70(1-2), 193-202. BSA (25-50 mg of) was dissolved in about 150 mg of ultra-pure water and emulsified with 2-3 ml of a solution of 50CP10C20-LL40 (15% w/v) or 30LP10L20-LL40 (23% w/v) in dichloromethane for 60 s using an Ultra turrax IKA T18 operated at 20 000 rpm yielding a water-in-oil (W/O) emulsion). The so-obtained primary emulsion was then emulsified in about 80-130 ml of UP-water containing 4.0 wt. % PVA for 30 s using an Ultra turrax IKA T18 operated at 14 000 rpm yielding a water-in-oil-in water (W/O/W) emulsion. The so-obtained secondary emulsion was gently stirred for 2 h at 600 rpm at room temperature. Due to the evaporation of the dichloromethane, the polymer precipitated from the solution to yield microspheres. After 3 h (the time necessary to achieve almost complete evaporation of the dichloromethane) the formed microspheres were collected by centrifugation, and the microspheres were washed three times with 100-200 ml of an aqueous solution of 0.05 wt. % Tween 20 in ultra-pure water. Finally, the microspheres were lyophilised.

For IVR tests, 2 ml of 100 mM phosphate buffer (pH 7.4, 0.02 wt. % NaN$_3$) in case of 30LP10L20-LL40 microspheres and 25 mM NaPi buffer (pH 7.2, 105 mM NaCl, 0.01 wt. % Tween 80, 0.02 wt. % NaN$_3$) in case of 50CP10C20-LL40 microspheres was added to 20 mg of microspheres. The sample was incubated at 37° C. and at each sampling point 1.8 ml of sample was taken and refreshed with release buffer. BSA content was measured with BCA protein assay in case of 30LP10L20-LL40 microspheres and with UPLC (eluent A: 1 wt. % TFA in UP-water, eluent B: 0.085 wt. % TFA in acetonitrile, 95/5 v/v A/B to 5/95 A/B in 25 min) in case of 50CP10C20-LL40 microspheres.

The particle size distribution of the microspheres was measured by Coulter counter. Approximately 1 mg of microspheres were dispersed in 50-100 ml of Isotron II solution by gently stirring and the particle size was measured with a Coulter counter equipped with a 100 µm measurement cell.

The BSA content of the microspheres was determined by dissolving 5-10 mg of microspheres, accurately weighted, in 5.0 ml of acetonitrile. After centrifugation, 4 ml of supernatant was removed and 5 ml of PBS was added. BSA content was measured with UPLC (eluent A: 0.1 wt. % TFA in UP-water, eluent B: 0.1 wt. % TFA in acetonitrile, 90/10 v/v A/B to 10/90 v/v A/B in 4 min).

Figure 6:
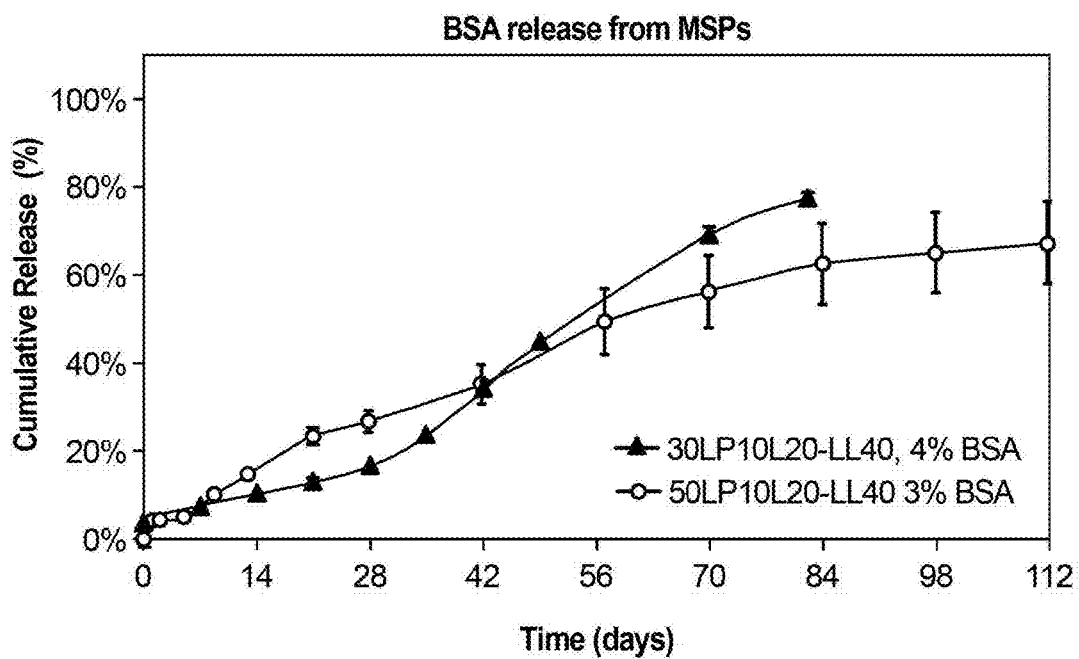
FIG. 6: In vitro release of BSA from microspheres composed of 30LP10L20-LL40 and 50CP10C20-LL40 loaded with 3-4 wt. % of BSA at 37° C. in phosphate buffer pH 7.4 (n=3).

Table 4 lists the particle size, encapsulation efficiency (EE) of the BSA loaded microspheres prepared. FIG. 6 shows the in vitro release of BSA from 30LP10L20-LL40 microspheres with 5 wt. % BSA target loading and 50CP10C20-LL40 microspheres with 10 wt. % BSA target loading. BSA was released from 30LP10L20-LL40 microspheres for almost 3 months in a linear fashion without significant burst. 50CP10C20-LL40 microspheres release BSA for almost ~3 months in a linear fashion without significant burst, where after slower release followed for another ~1.5 months.

TABLE 4

Average particle size, BSA content and encapsulation efficiency of BSA loaded 50CP10C20-LL40 and 30LP10L20-LL40 microspheres.

| Polymer grade | Average size (µm) | Content (wt. %) | EE (%) |
|---|---|---|---|
| 50CP10C20-LL40 | 14 | 2.8 | 33 |
| 30LP10L20-LL40 | 18 | 4.3 | 85 |

Example 18

In this example various hydrophilic phase separated multi-block copolymers prepared as described in the examples above were used to prepare Insulin-like Growth Factor I (IGF-1) loaded film and microsphere formulations.

IGF-1 loaded films were prepared by dissolution of 0.18 g of polymer into 1.46 g of dichloromethane and subsequent emulsification by Ultra turraxing with IGF-1 dissolved in ultra pure water at 18 000 rpm for 30 s or by using ultrasound at 100 W for 5 s. The emulsion was poured into a Teflon™ mould. Dichloromethane was left to evaporate overnight and residual dichloromethane was removed by vacuum drying overnight. 20 mg films were cut and put on release at 37° C. with 1 ml of phosphate buffered saline (PBS, 25 M pH 7.2, 105 mM NaCl, 0.01 wt. % Tween 80 and 0.02 wt. % NaN$_3$). At predetermined time points, samples were taken and the sampled amount was refreshed by fresh buffer.

IGF-1 loaded microspheres were prepared by a solvent extraction/evaporation based W/O/W emulsification process. 2.78 mg of IGF-1 and 51.8 mg of BSA were dissolved in 143 µl of UP-water in an Eppendorf cup and emulsified in a solution of 0.47 g of 50CP10C20-LL40 (IV 1.05 dl/g) in 2.62 g of dichloromethane using an Ultra turrax (20 000 rpm, 60 s). The so-obtained primary emulsion was then emulsified in 81 ml of UP-water containing 4.0 wt. % PVA using an Ultra turrax (14 000 rpm for 60 s), and stirred for 2 h at 600 rpm at room temperature. The resulting microspheres were collected on a 5 µm membrane filter and washed with 1 l of UP-water containing 0.05 wt. % Tween 80. Finally, the microspheres were lyophilised.

Approximately 1 mg of microspheres were dispersed in 50-100 ml of Isotron II solution by gently stirring and the particle size was measured with a Coulter counter equipped with a 100 µm measurement cell.

The IGF-1 and BSA content were determined by dissolving 5 mg of microspheres, accurately weighted, in 0.3 ml of acetonitrile. Subsequently, 1.2 ml of PBS was added and gently shaken. After centrifugation, the IGF-1 and BSA content in the supernatant were determined by UPLC. Procedure was performed in triplicate.

Using a commercial sandwich ELISA (R&D Systems), the concentration of human insulin-like Growth Factor I (IGF-1) in a sample was measured to confirm that micro-encapsulated and released IGF-1 was still capable to bind with the capture and detection antibody after release and thus no protein degradation at that level has occurred. The capture and detection antibody of the kit were specific for natural and recombinant IGF-1 and as a standard recombinant IGF-1.

To investigate the structural integrity of released IGF-1, 100-300 ng of IGF-1 collected from release samples was denaturated using Laemli/β-mercapto-ethanol buffer and loaded on an 'any KD TGX' pre-cast mini gel and separated under denaturating conditions at 100-200 V using 1× Tris/Glycine/SDS as separating buffer, and stained overnight in colloidal CBB staining agent. A Dual Xtra Protein marker (Bio-Rad) was used to determine the protein size of the separated proteins.

Figure 7:
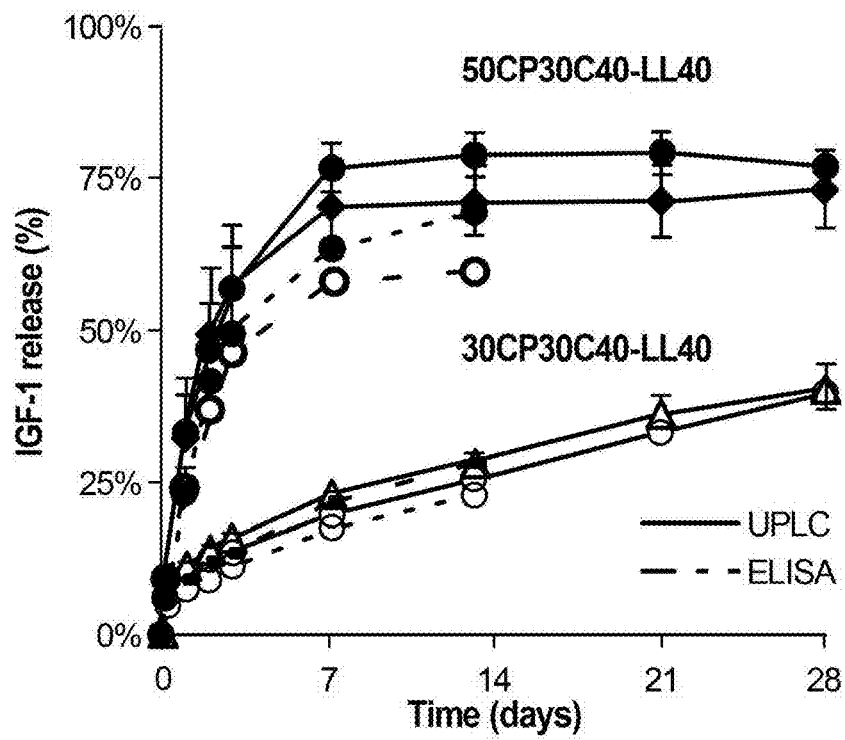
FIG. 7: In vitro release of IGF-1 from IGF-1 loaded 50CP30C40-LL40 and 30CP30C40-LL40 films made by solvent casting of W/O. Release was measured at 37° C. in phosphate buffer pH 7.2 (n=3). Solid lines represent IGF-1 release as measured by UPLC. Dotted lines represent IGF-1 release as measured by ELISA.

FIG. 7 shows the in vitro release of IGF-1 from 50CP30C40-LL40 and 30CP30C40-LL40 polymer films loaded with 0.6 wt. % of IGF-1 as measured by UPLC and ELISA. IGF-1 was released from the 50CP30C40-LL40 films in about 7 days whereas IGF-1 was slowly released from the 30CP30C40-LL40 polymer films with a cumulative release of about 40% after 28 days. Since the cumulative release of IGF-1 as measured by UPLC was nearly identical to the cumulative release of IGF-1 as measured by ELISA it was concluded that the released IGF-1 was structurally intact and biologically active.

Figure 8:
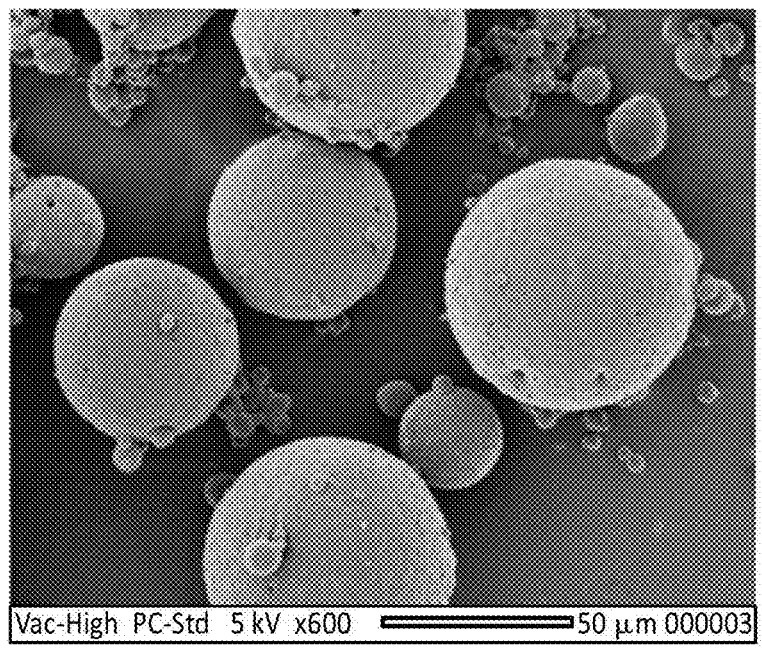
FIG. 8: SEM photo of 0.2 wt. % IGF-1 loaded 50CP10C20-LL40 microspheres prepared via a W/O/W double emulsion route.
Figure 9:
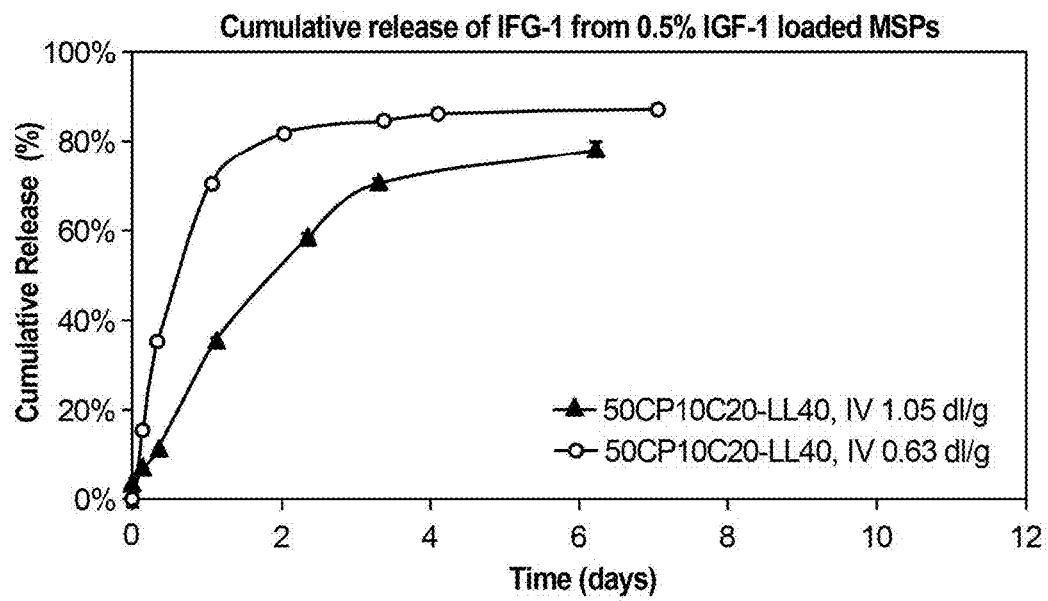
FIG. 9: In vitro release of IGF-1 from 0.2 wt. % IGF-1 loaded microspheres prepared of 50CP10C20-LL40 with different IVs. Release was measured at 37° C. in phosphate buffer pH 7.2 (n=3).
Figure 10:
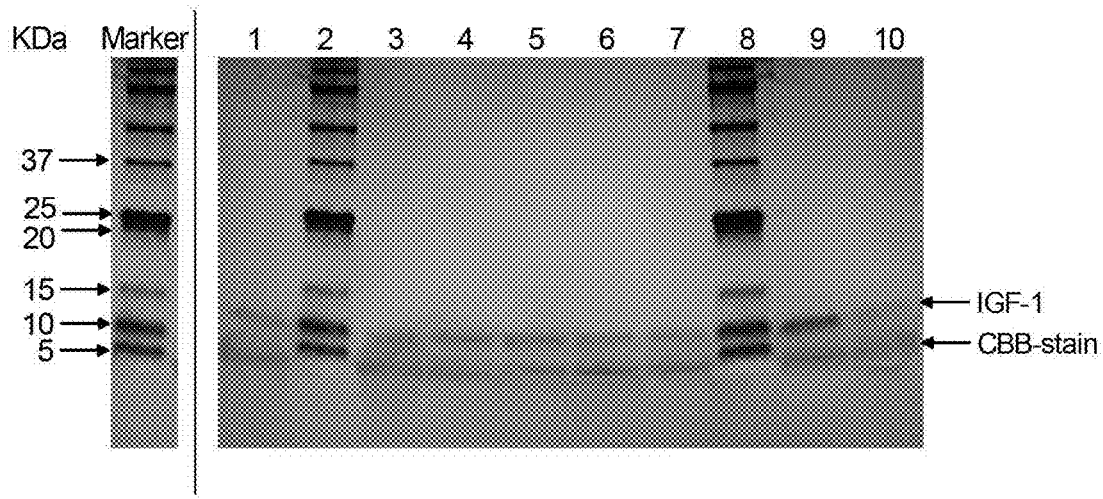
FIG. 10: SDS PAGE results of IGF-1 released from 50CP10C20-LL40 microspheres with 0.2 wt % IGF-1 target loading and prepared using various ultra-turrax speeds after 1 and 2 weeks.

Microspheres with 0.5 wt. % of IGF-1 target loadings were prepared of 50CP10C20-LL40 with IV 1.05 and 0.68 dl/g by a double emulsification process. The microspheres had a smooth surface (FIG. 8) and encapsulation efficiencies varying between 40 and 60%. The volume average particle size ($d_{50}$) as measured with a Coulter counter equipped with a 100 µm measurement cell was 54.4 µm with a CV (coefficient of variation) of 61%. FIG. 9 shows IGF-1 release from these microspheres in vitro. Complete release of IGF-1 within 2 days was obtained for microspheres composed of 50CP10C20-LL40 with IV 0.68 dl/g. IGF-1 release from microspheres composed of 50CP10C20-LL40 with IV 1.05 dl/g was slower with complete release achieved after approximately 6 days. Released IGF-1 was structurally intact as could be concluded from the SDS-PAGE results (FIG. 10), which did not show any degradation nor aggregation of the protein.

Example 19

In this example various hydrophilic phase separated multi-block copolymers (20LP10L20-LL40 (IV 0.58 dl/g), 30LP6L20-LL40 (IV 0.60 dl/g) and 30CP10C20-LL40 (IV 0.71 dl/g)) prepared as described in the examples above were used to prepare film formulations loaded with a highly water-soluble biologically active polypeptide with a molecular weight of 15 kDa (Protein A). Furthermore, 30CP10C20-LL40 multi-block copolymers with various IV (0.81, 0.71 and 0.65 dl/g) were used to formulate Protein A into microspheres formulations.

Protein A loaded films were prepared by a solvent casting method. 10 mg of Protein A was dissolved in 123 mg of UP-water and emulsified in a solution of 0.18 g of polymer in 1.46 g of dichloromethane using an Ultra turrax (18 000 rpm, 60 s). The so-obtained primary emulsion was poured in a Teflon™ mould and the dichloromethane was evaporated overnight. Residual dichloromethane was removed by vacuum drying.

Protein A loaded microspheres were prepared by a solvent extraction/evaporation based W/O/W emulsification process. 21 mg of Protein A (5 wt. % target loading) was dissolved in 156 µl of UP-water optionally containing inulin in an Eppendorf cup and emulsified in a solution of 0.4 g of polymer in 2.1 g of dichloromethane using an Ultra turrax (20 000 rpm, 60 s). The so-obtained primary emulsion was then emulsified in 70 ml of UP-water containing 4.0 wt. % PVA using an ultraturrax (14 000 rpm for 60 s), and stirred for 2 h at 600 rpm at room temperature. The resulting microspheres were collected on a 5 µm membrane filter and washed with three times 100 ml of UP-water containing 0.05 wt. % Tween 80. Finally, the microspheres were lyophilised.

Approximately 10 mg of microspheres were dispersed in 50-100 ml of Isotron II solution by gently stirring and the particle size was measured with a Coulter counter equipped with a 100 µm measurement cell.

The Protein A content was determined by dissolving 5 mg of microspheres, accurately weighted, in 0.3 ml of acetonitrile. After centrifugation, the supernatant was removed and the residual ACN was evaporated. 1.95 ml of PBS was added. Protein A content was measured with UPLC (eluent A: 0.1 wt. % TFA in UP-water, eluent B: 0.1 wt. % TFA in acetonitrile, 80/20 v/v A/B to 10/90 A/B in 3 min).

For SEM imaging, a small amount of microspheres was adhered to carbon conductive tape and coated with gold for 3 min. The sample was imaged using a 10 kV electron beam.

The in vitro release kinetics of Protein A-loaded films and microspheres were measured in 100 mM of phosphate buffer pH 7.4 (20 mg of film in 2 ml). The samples were incubated at 37° C. At each sampling point, 1.8 nil of sample was taken and refreshed with 1.8 ml of phosphate buffer. Protein A content was measured with UPLC (eluent A: 0.1 wt. % TFA in UP-water, eluent B: 0.1 wt. % TFA in acetonitrile, 80/20 v/v A/B to 10/90 AB in 3 min).

SDS-PAGE was performed in reducing mode with 4-20% Tris-HCl gels. Per slot 20 µl of protein solution was applied for samples and Protein A standard. For the marker, 2 µl was applied to the slot. The amount of protein added per slot was either 75 or 150 ng. Samples were prepared by dilution with 12 mM PBS pH 7.4 or UP-water to a Protein A concentration of either 150 or 300 ng/20 µl. Subsequently, Laemmli working solution (Laemmli buffer containing 1% of mer-captoethanol) was added in ratio 1:1 v/v. The samples were heated to ~90° C. for 5 min and applied to the gels. The gels were clamped in the electrophoresis cell and running buffer (Tris/Glycine/SDS pH 8.3) was added. The samples and standards were applied to the gels, and the gels were run for 15 min at 100 kV. The voltage was subsequently set to 200 kV and the gels were run until a good separation of the molecular weight standards was obtained. The gels were washed with UP-water and stained with silver reagent.

Figure 11:
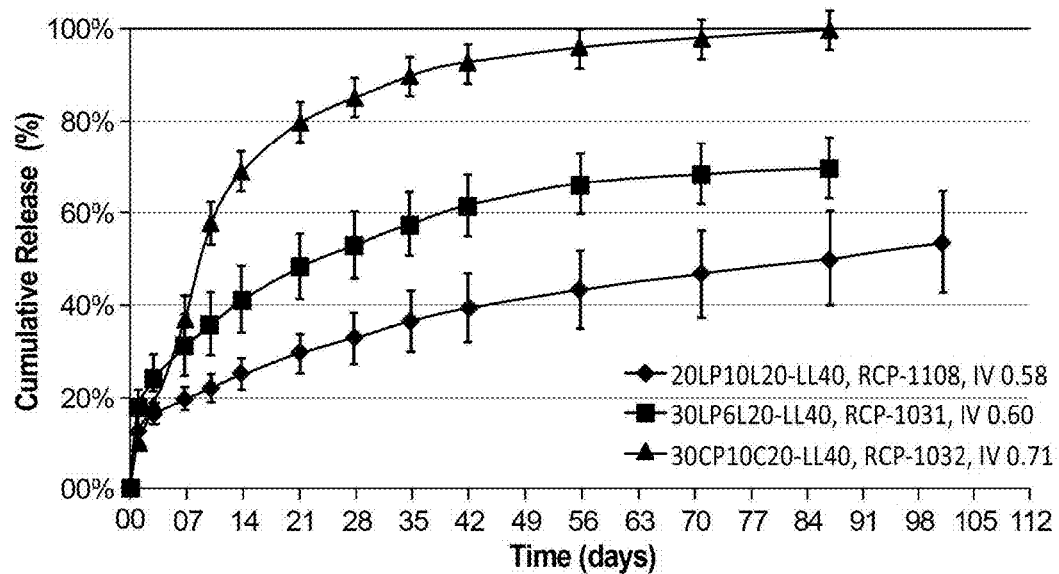
FIG. 11: In vitro release Protein A (MW 15 000 Da) from films composed of 20LP10L20-LL40, 30LP6L20-LL40 and 30CP10C20-LL40 (Protein A content 5 wt. %; film thickness 80-120 μm). Release was measured at 37° C. in phosphate buffer pH 7.4 (n=3).
Figure 12:
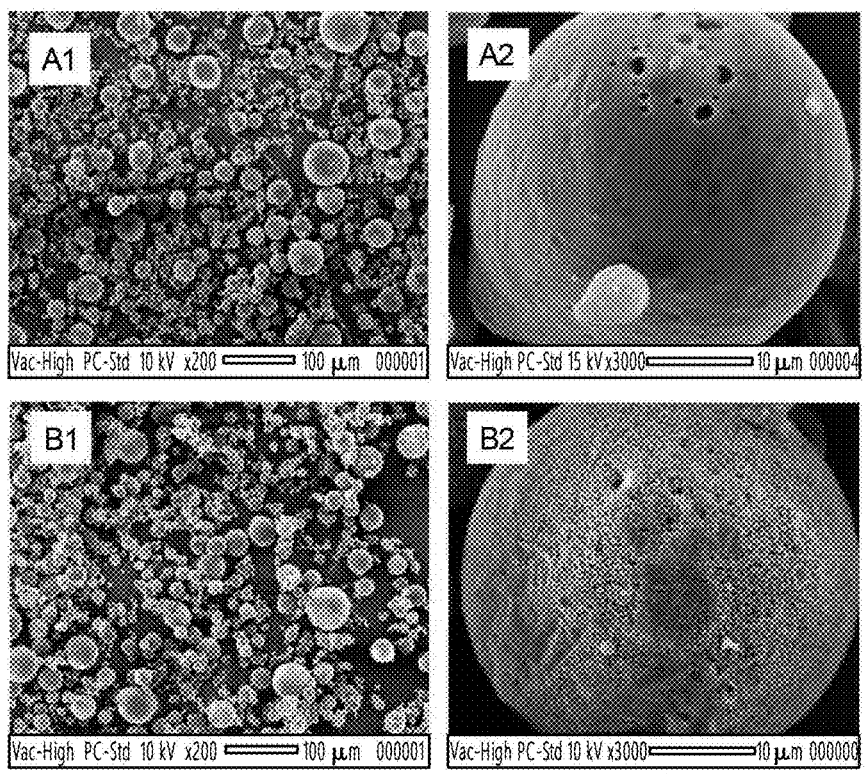
Figure 13:
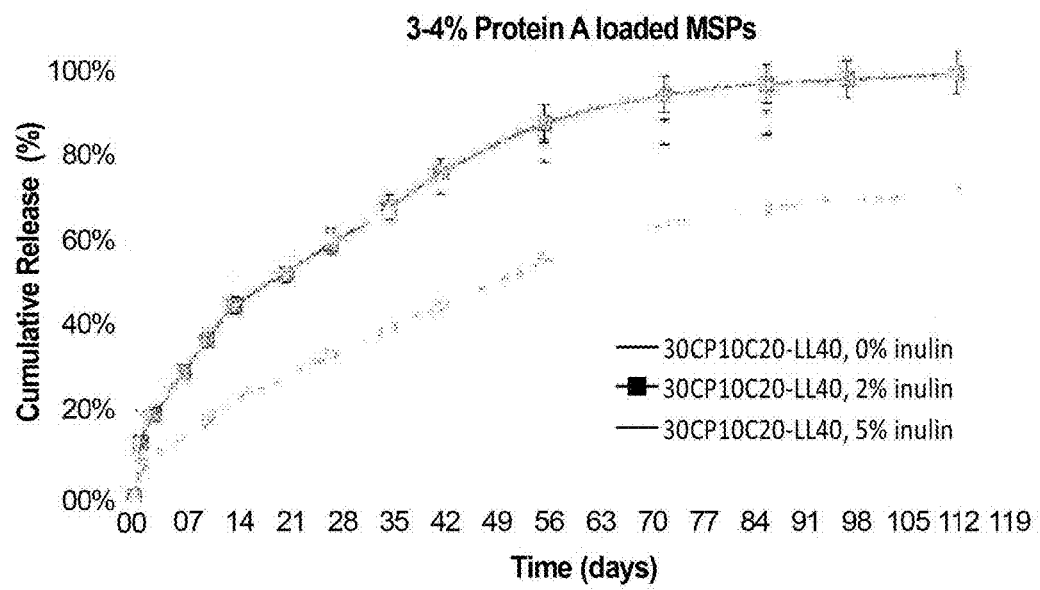
FIG. 13: In vitro release of Protein A from microspheres composed of 30CP10C20-LL40 at 3-4 wt. % Protein A target loading with optionally 2 or 5 wt. % of inulin co-encapsulated, at 37° C. in phosphate buffer pH 7.4 (n=3).
Figure 14:
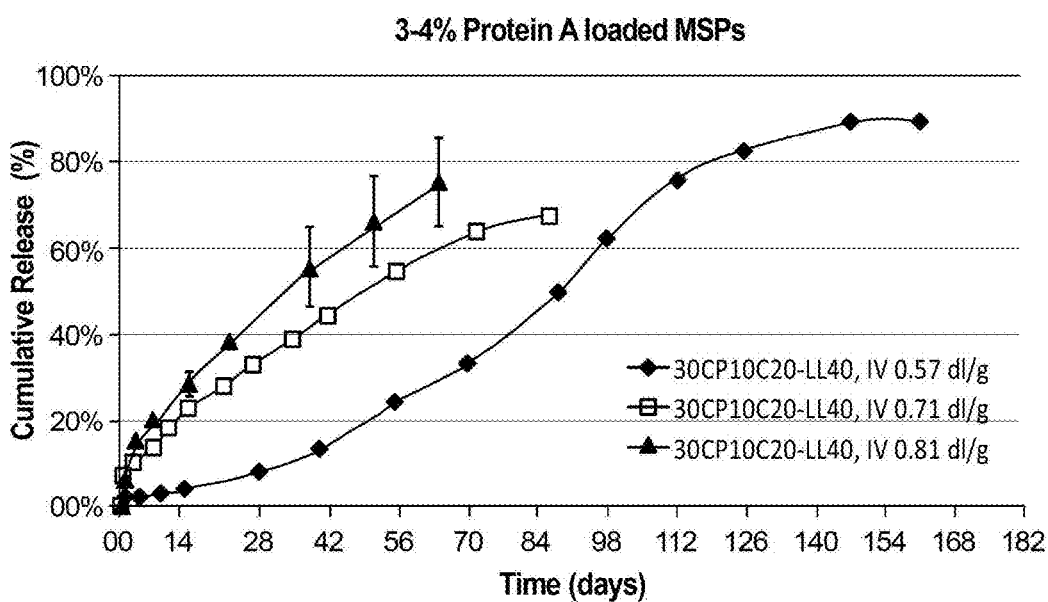
FIG. 14: In vitro release of Protein A from microspheres composed of 30CP10C20-LL40 at 3-4 wt. % Protein A target loading and different polymer IV, at 37° C. in phosphate buffer pH 7.4 (n=3).
Figure 15:
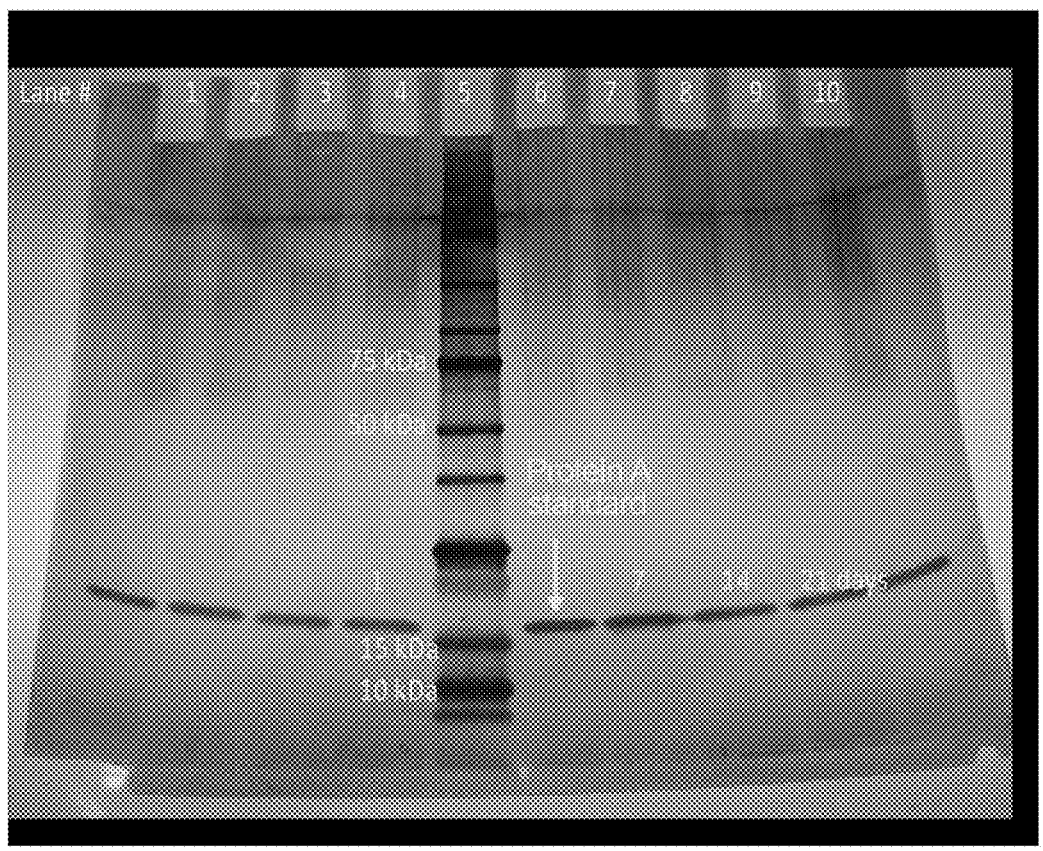
FIG. 15: SDS-PAGE results of Protein A released from 30CP10C20-LL40 microspheres with 4 wt. % Protein A and 2 wt. % inulin target loading after 1 (lane 4), 7 (lane 7), 14 (lane 8) and 21 (lane 9) days. Lane 5: Molecular weight markers. Lane 6: Protein A standard. Note that the dark smears are due to colouring of phosphate buffer salts.

FIG. 11 shows the in vitro release of Protein A from 20LP10L20-LL40 (10 wt. % of PEG MW 1000), 30LP6L20-LL40 (9 wt. % of PEG MW 600) and 30CP10C20-LL40 (15 wt. % of PEG MW 1000). 30CP10C20-LL40-based films released Protein A relatively fast with a cumulative release of Protein A of 100% after 3 months. By replacing PEG1000 by PEG600, which leads to reduction of the swelling degree, the release of Protein A could be slowed down and near first-order diffusion controlled release kinetics were obtained leading to a cumulative release of ~75% after 4 months. Reduction of the release rate of Protein A could also be achieved by lowering the weight fraction of the hydrophilic LP10L20 block in the polymer. By using 20LP10L20-LL40 (10 wt. % PEG1000) release could be further slowed down, and after an initial small burst of less than 15%, well-controlled release kinetics of Protein A were obtained with cumulative release of ~65% in 6 months. The data clearly show that Protein A release kinetics can be controlled by the choice of polymer.

Protein-A-loaded microspheres were prepared of 30CP10C20-LL40 loaded with 3-4 wt. % of Protein A. Optionally, 2 or 5 wt. % of inulin was co-encapsulated to enhance the release rate of Protein A. The effect of polymer molecular weight on protein release kinetics was studied by studying the release kinetics of Protein A from microspheres composed of 30CP10C20-LL40 polymers with different intrinsic viscosity. For all Protein A loaded microspheres, spherical microspheres were obtained. For microspheres with co-encapsulated inulin, the surface porosity increased with increasing inulin content, as shown on the SEM pictures in FIG. 12. Table 5 lists the particle size and encapsulation efficiency (EE) of Protein A of the microspheres. FIG. 13 shows that after a small initial burst, Protein A was released at a constant rate. It was observed that the burst decreased and linearity increased with decreasing inulin content. Without inulin present ~70% was released in 3 months, while 90-100% was released when 2 or 5 wt. % inulin was co-encapsulated. Release of Protein A from 30CP10C20-LL40 films containing 2 or 5 wt. % of co-encapsulated inulin were similar. Release data is shown up to ~4 months. Expected duration of release for Protein A from 30CP10C20-LL40 microspheres is approximately 6 months.

FIG. 14 shows the release kinetics of Protein A from 30CP10C20-LL40 films with different intrinsic viscosity (IV) of the polymer. The release rate of Protein A increased with increasing polymer IV. For 30CP10C20-LL40 polymers with an IV 0.71 or 0.81 dl/g, sustained release of Protein A was obtained with cumulative release of 60-70% after 2 months. The release kinetics of Protein A from microspheres composed of 30CP10C20-LL40 with an IV of 0.58 dl/g were significantly different. The initial release rate up to one month was significantly lower, but Protein A release accelerated between 1 and 3 months, where after it slowed down again, giving a total duration of release of approximately 5 months. The data clearly show that Protein A can be released from microspheres in linear fashion for at least 4 months and that release kinetics can be controlled by the co-encapsulation of sugars, such as inulin, as well as by the intrinsic viscosity of the polymer.

The structural integrity of Protein A released from microspheres was studied by SDS-PAGE. SDS-PAGE confirmed that Protein A released for at least 21 days consisted mainly of native Protein (FIG. 15). These results show that 30CP10C20-LL40 microspheres provide a suitable matrix for the long-term release of structurally intact Protein A.

TABLE 5

Overview of Protein A loaded microspheres characteristics with 3-4 wt. % Protein A target loading.

| MSP # | Polymer IV (dl/g) | Co-encapsulated inulin (wt. %) | Particle size (μm) | Protein A content (wt. %) | EE Protein A (%) |
|---|---|---|---|---|---|
| #1 | 0.71 | 0 | 52 | 3.7 | 100 |
| #2 | 0.71 | 2 | 57 | 3.3 | 90 |
| #3 | 0.71 | 5 | 55 | 1.8 | 54 |
| #4 | 0.57 | 0 | 33 | 4.0 | 100 |
| #5 | 0.81 | 0 | 43 | 0.7 | 24 |

Example 20

In this example the hydrophilic phase separated multiblock copolymer 20LP10L20-LL40 (IV 0.73 dl/g) prepared as described in the examples above was used to prepare film and microsphere formulations loaded with a biologically active polypeptide with a molecular weight of 2.5 kDa (Peptide A).

Peptide A loaded films were prepared by a solvent casting method. 10 (for 5 wt. % loading) or 20 mg (for 10 wt. % loading) of Peptide A was dissolved in 123 mg of UP-water and emulsified in a solution of 0.18 g of 20LP10L20-LL40 (IV 0.76 dl/g) in 1.46 g of dichloromethane using an Ultra turrax (18 000 rpm, 30 s). The so-obtained primary emulsion was poured in a Teflon mould and the dichloromethane was evaporated overnight. Residual dichloromethane was removed by vacuum drying.

Peptide A loaded microspheres were prepared by a solvent evaporation based double emulsion process. 50 mg of Peptide A was dissolved in PBS and emulsified in a solution of 0.5 g of 20LP10L20-LL40 (IV 0.73 dl/g) in 2 g of dichloromethane using an Ultra turrax (24 000 rpm, 60 s). The so-obtained primary emulsion was then emulsified in 200 ml of UP-water containing 4.0 wt. % polyvinyl alcohol using an ultraturrax (14 000 rpm for 30 s), and stirred for 3 h at 600 rpm at room temperature. The resulting microspheres were centrifuged, the supernatant was removed and the microspheres were washed three times with 200 ml of UP-water containing 0.05 wt. % Tween 20. Finally, the microspheres were lyophilised. The particle size distribution was measured with a Coulter Counter. Approximately 10 mg of microspheres were dispersed in 50-100 ml of Isotron II solution by gently stirring and the particle size was measured with a 100 μm measurement cell.

Peptide A content of microspheres was determined by dissolving 5-10 mg of microspheres, accurately weighted, in 5.0 ml of acetonitrile. After centrifugation, 4 ml of supernatant was removed and 5 ml of PBS was added. Peptide A content was measured with HPLC (eluent A: 1 wt. % TFA in UP-water, eluent B: 0.085 wt. % TFA in acetonitrile, 95/5 v/v A/B to 5/95 A/B in 25 min).

The in vitro release kinetics of Peptide A from films and microspheres were measured in PBS pH at 37° C. Peptide A containing films or microspheres (5-20 mg) were weighed into a vial and 2 ml of PBS was added. The vials were incubated at 37° C. and sampled at pre-determined timepoints. At each sampling point 75-90% of release medium was collected and replaced by fresh PBS. Peptide A content of release samples was determined with HPLC (eluent A: 1 wt. % TFA in UP-water, eluent B: 0.085 wt. % TFA in acetonitrile, 95/5 v/v A/B to 5/95 A/B in 25 min).

Figure 16:
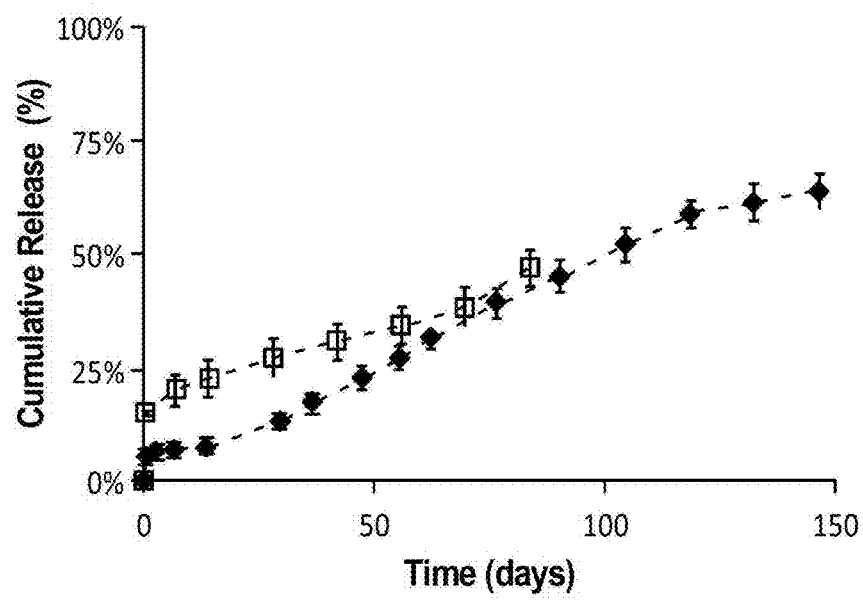
FIG. 16: In vitro release of Peptide A (MW 2500) from films composed of 20LP10L20-LL40 (peptide load 5 and 10 wt. %; film thickness 80-100 μm) loaded. Release was measured at 37° C. in phosphate buffer pH 7.4 (n=3).

FIG. 16 shows the in vitro release of Peptide A from 20LP10L20-LL40 films. Peptide A was released from 5 wt. % loaded 20LP10L20-LL40 films in a linear fashion for at least 5 months without significant burst. For 20LP10L20-LL40 films with a higher Peptide A loading (10 wt. %), burst release increased to 15%. After approximately 2 months, release was similar to the 5 wt. % loaded films.

Figure 17:
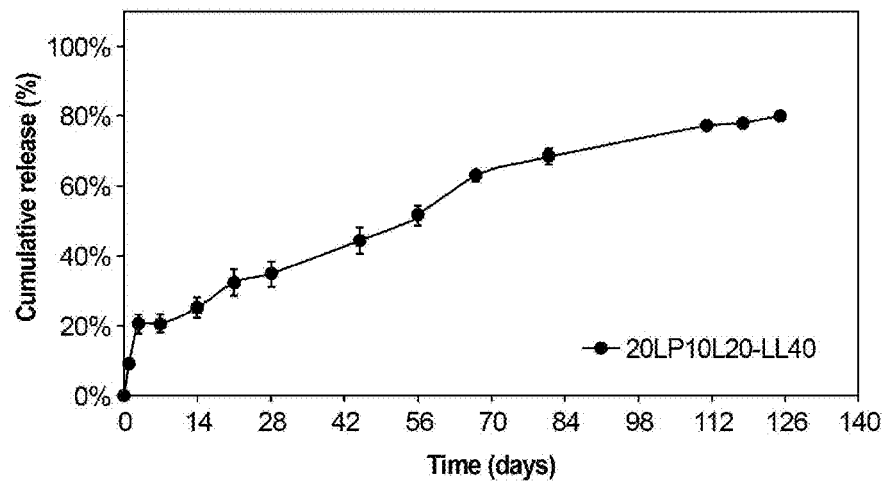
FIG. 17: In vitro release of Peptide A (MW 2500) from microspheres composed of 20LP10L20-LL40 (particle size 30 μm; peptide load 10 wt. %). Release was measured at 37° C. in phosphate buffer pH 7.4 (n=3).

Peptide A loaded 20LP10L20-LL40 microspheres had an average particle size of 30 µm and a Peptide A content of 10.3 wt. %, representing an encapsulation efficiency of 100%. FIG. 17 shows that Peptide A MSP exhibited a low burst release of approximately 10 wt. % followed by zero-order release kinetics for at least 40 days.

Example 21

In this example, hydrophilic phase separated multi-block copolymers 20LP10L20-LL40 (Example 8) and 10LP10L20-LL40 were used to prepare microspheres loaded with rapamycin (MW 914 Da). The polyethylene glycol component of the polymers had a molecular weight of 1000 g/mol.

Rapamycin loaded microspheres with a target load of 20 wt. % rapamycin were prepared by a solvent evaporation method using a single oil-in-water (O/W) emulsion route. The polymers were dissolved in various blend ratios in dichloromethane to a concentration of about 20 wt. %, and the required amount of rapamycin was added. The polymer/rapamycin solution was then emulsified in 200 ml of UP-water containing 4.0 wt. % polyvinyl alcohol (PVA) using an Ultra turrax (14 000 rpm for 30 s), and then stirred with a magnetic stirrer for 3 h at 300 rpm at room temperature. The microsphere dispersion was concentrated by centrifugation and the microspheres were washed three times with 50 ml of aqueous 0.05 wt. % Tween 20 solution. Finally, the microspheres were lyophilised.

The particle size distribution was measured with a Coulter Counter. Approximately 10 mg of microspheres were dispersed in 50-100 ml of Isotron II solution by gently stirring and the particle size was measured with a 100 µm measurement cell.

Rapamycin content of microspheres was determined by dissolving 5-10 mg of microspheres, accurately weighted, in 5.0 ml of acetonitrile. After centrifugation, 4 ml of supernatant was removed and 5 ml of PBS was added. Rapamycin content was measured with HPLC (eluens: acetonitrile/water 70/30 v/v; 278 nm).

The in vitro release kinetics of rapamycin from microspheres were measured at 37° C. in 10 mM PBS pH 7.4 containing 0.5 wt. % SDS rapamycin containing microspheres (5-20 mg) were weighed into a vial and 2 ml of release medium was added. The vials were incubated at 37° C. and sampled at pre-determined time-points. At each sampling point 75-90% of release medium was collected and replaced by fresh PBS. Rapamycin content of release samples was determined with HPLC.

Figure 18:
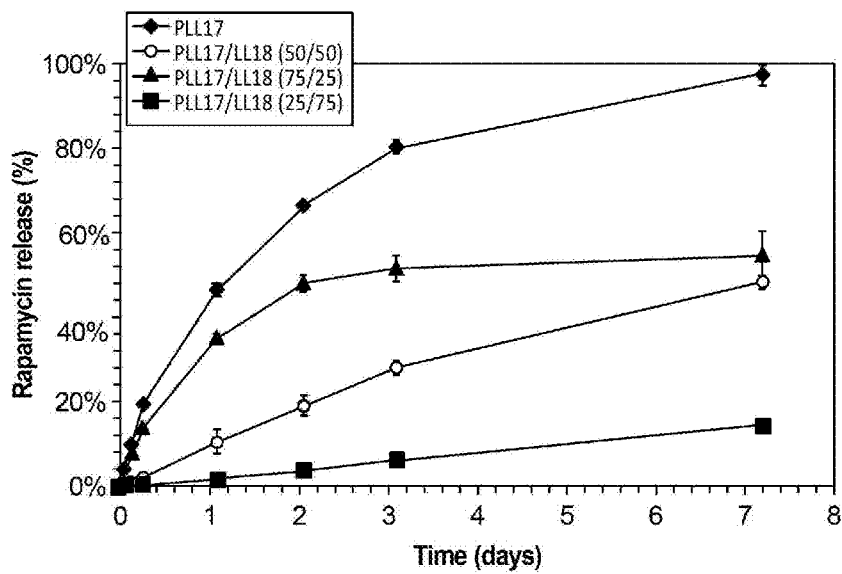
FIG. 18 In vitro release of rapamycin from microspheres composed of various blends of 20LP1020-LL40- and 10LP10L20-LL40.

The so-prepared rapamycin microspheres had an average size of 35 µm and a rapamycin content varying from 17 to 20 wt. %, representing encapsulation efficiencies of 89% to 100%. FIG. 18 shows the release of rapamycin from microspheres composed of various blends of 20LP10L20-LL40 and 10LP10L20-LL40. Rapamycin release from 20LP10L20-LL40-based microspheres was relatively fast, whereas release of rapamycin from 10LP10L20-LL40-based microspheres was very slow. By blending the two polymers microspheres with intermediate release profiles were obtained.

Example 22

In this example, goserelin acetate loaded microspheres were prepared of the hydrophilic phase separated multi-block copolymer 20LP10L20-LL40 by means of a water-in-oil-in-oil process. 62.6 mg of goserelin acetate was dissolved in 150 µl of UP-water (29.4 wt. %) and emulsified with a solution of 0.5 g of 20LP10-LLA40 polymer in 7.4 g of dichloromethane in a scintillation vial (Ultra turrax, 20 000 rpm, 60 s). 13.5 g of the polymer precipitant (silicon oil, 350 cSt) was then slowly added (2-5 min) under constant stirring (12 000 rpm) to form embryonic microparticles. The embryonic microparticles were then poured into 550 ml of heptane at room temperature (13.5:1 ratio of dichloromethane to heptane solvent). The extraction vessel was closed to prevent excessive evaporation of the extraction medium. After approximately 3 h of extraction, the microparticles were collected by vacuum filtration, rinsed with additional heptane and dried under vacuum. The microspheres had an average size of 67 µm and a goserelin content of 8.3%, representing an encapsulation efficiency of 88%.

The particle size distribution was measured with a Coulter Counter. Approximately 10 mg of microspheres were dispersed in 50-100 ml of Isotron II solution by gently stirring and the particle size was measured with a 100 µm measurement cell.

Goserelin content of microspheres was determined by dissolving 5-10 mg of microspheres, accurately weighted, in 5.0 ml of acetonitrile. After centrifugation, 4 ml of supernatant was removed and 5 ml of PBS was added. Goserelin content was measured with HPLC (eluens: water/acetonitrile/trifluoracetic acid 72/28/0.1, 220 nm).

The in vitro release kinetics of goserelin from microspheres were measured in PBS (192 mM pH 7.4 containing 0.01% tween 80 and 0.02% sodium azide) at 37° C. Goserelin containing microspheres (5-20 mg) were weighed into a vial and 2 ml of release medium was added. The vials were incubated at 37° C. and sampled at pre-determined time-points. At each sampling point 75-90% of release medium was collected and replaced by fresh PBS. Goserelin content of release samples was determined with HPLC.

Figure 19:
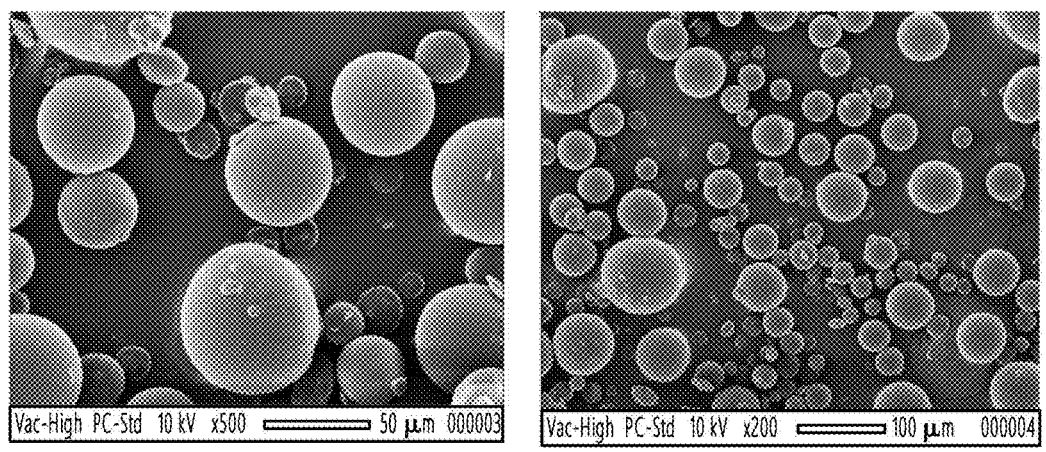
FIG. 19 SEM pictures of goserelin-loaded 20LP1020-LL40 microspheres prepared via the W/O/O method FIG. 20 In vitro release of goserelin from 20LP1020-LL40 microspheres prepared via the W/O/O method
Figure 20:
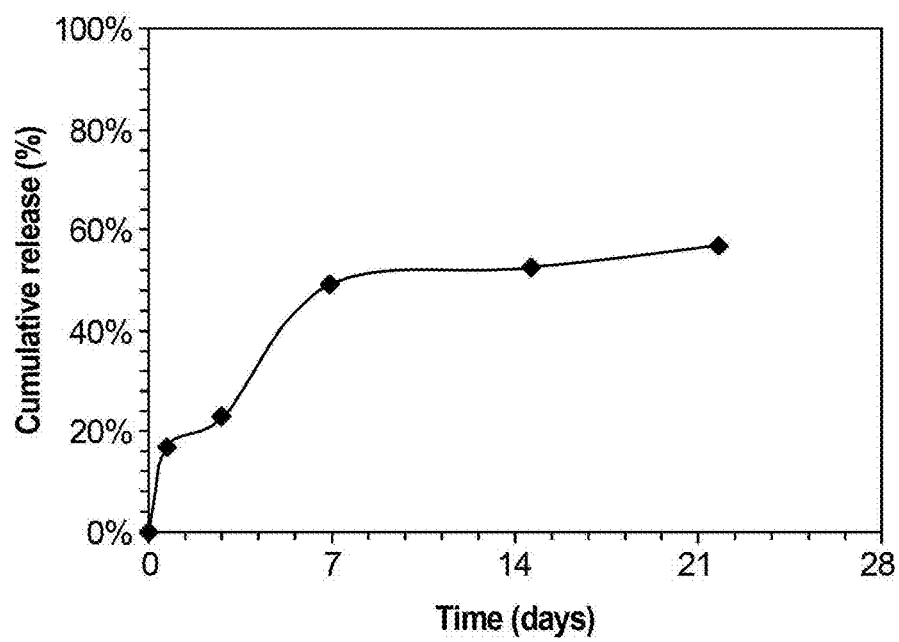

The so-prepared goserelin-loaded 20LP10-LLa40 microspheres had a spherical and smooth appearance (FIG. 19), an average size of 71 µM (CV 47%) and a goserelin content of 8.3% representing an encapsulation efficiency of 88%. FIG. 20 shows the release of goserelin from the microspheres.

Example 23

In this example, lysozyme-loaded microspheres were prepared of the hydrophilic phase separated multi-block copolymer 30CP10L20-LL40 by means of a solid-in-oil-in-oil process (S/O/O). 0.43 g of 30CP10L20-LL40 was dissolved in 7.4 g of dichloromethane in a scintillation vial (5.4 wt. %), and 0.074 g of spray-dried inulin-stabilized lysozyme microparticles (lysozyme/inulin ratio: 1:2 w/w) with a particle size of 1-2 µm were added to the polymer solution, and the dispersion was homogenised by Ultra turrax (20 000 rpm, 60 s). 11.46 g of the polymer precipitant (silicon oil, 350 cSt) was then slowly added (2-5 min) under constant stirring (12 000 rpm) to form embryonic microparticles. The embryonic microparticles were then poured into 550 ml of heptane at room temperature (13.5:1 ratio of dichloromethane to heptane solvent). The extraction vessel was closed to prevent excessive evaporation of the extraction medium. After approximately 3 h of extraction, the microparticles were collected by vacuum filtration, rinsed with additional heptanes and dried by vacuum filtration. The microspheres had an average size of 59 μm and a lysozyme content of 4.1-5.6%, representing an encapsulation efficiency of 80-100%.

The invention claimed is:

1. Biodegradable, semi-crystalline, phase separated, thermoplastic multi-block copolymer, the copolymer being characterised in that:
    a) it comprises at least one hydrolysable pre-polymer (A) segment and at least one hydrolysable pre-polymer (B) segment,
    b) said multi-block copolymer having a Tg of 37° C. or less and a Tm of 110-250° C. under physiological conditions;
    c) the segments are linked by a multifunctional chain-extender, wherein said chain extender is a diisocyanate;
    d) the segments are randomly distributed over the polymer chain;
    e) at least part of the pre-polymer (A) segment is derived from a water-soluble polymer, and
    wherein said pre-polymer (B) segment has a Tm of 110-250° C. and is based on poly(l-lactic acid), poly (d-lactic acid), polyglycolic acid, or combinations thereof, and
    wherein said water-soluble polymer is derived from poly(ethylene glycol) (PEG).

2. Biodegradable, semi-crystalline, phase separated, thermoplastic multi-block copolymer according to claim 1, wherein said chain-extender is a difunctional aliphatic chain-extender.

3. Biodegradable, semi-crystalline, phase separated, thermoplastic multi-block copolymer according to claim 1, wherein pre-polymer (A) comprises reaction products of cyclic monomers and/or non cyclic monomers.

4. Biodegradable, semi-crystalline, phase separated, thermoplastic multi-block copolymer according to claim 1, wherein a water-soluble polymer is present as an additional pre-polymer.

5. Biodegradable, semi-crystalline, phase separated, thermoplastic multi-block copolymer according to claim 1, wherein said pre-polymer (B) segment comprises a crystallisable polymer derived from hydroxyalkanoate, glycolide, l-lactide or d-lactide.

6. Biodegradable, semi-crystalline, phase separated, thermoplastic multi-block copolymer according to claim 1, having a swelling ratio under physiological conditions varies from 1 to 4.

7. Biodegradable, semi-crystalline, phase separated, thermoplastic multi-block copolymer according to claim 1, wherein said copolymer has an intrinsic viscosity of at least 0.1 dl/g.

8. A composition for the delivery of at least one biologically active compound to a host, comprising at least one biologically active compound encapsulated in a matrix, wherein said matrix comprises at least one biodegradable, semi-crystalline, phase separated, thermoplastic multi-block copolymer according to claim 1.

9. A composition according to claim 8, wherein said at least one biologically active compound is a non-peptide non-protein small sized drug, or a biologically active polypeptide.

10. A composition according to claim 9, wherein said non-peptide, non-protein small sized drug comprises one or more selected from the group consisting of an anti-tumour agent, an anti-microbial agent, a sephalosporin, an aminoglycoside, a macrolide, a tetracycline, a chemotherapeutic agent, a urinary tract antiseptic, a drug for anaerobic infections, a drug for tuberculosis, a drug for leprosy, an anti-fungal agent, an antiviral agent, an anti-helminthiasis agent, an anti-inflammatory agent, an anti-gout agent, a centrally acting (opoid) analgesic, a local anaesthetic, a drug for Parkinson's disease, a centrally acting muscle relaxant, a hormone or hormone anti-agonist, a corticosteroid, a glucocorticosteroid, an androgen, an androgenic steroid, an anabolic steroid, an anti-androgen, an estrogen, an estrogenic steroid, an anti-estrogen, a progestin, a thyroid drug and an anti-thyroid drug.

11. A composition according to claim 9, wherein said biologically active polypeptide comprises one or more selected from the group consisting of a protein/peptide drug, an enzyme, a receptor ligand, a neurotransmitter, an inhibitory peptide, a regulatory peptide, an activator peptide, a cytokine, a growth factor, a monoclonal antibody, a monoclonal antibody fragment, an anti-tumour peptide, an antibiotic, an antigen, a vaccine, and a hormone.

12. Composition according to claim 8, wherein said biologically active compound is a non-peptide, non-protein small molecule having an Mn which is 1000 Da or less, preferably said multi-block copolymer contains poly(ethylene glycol), as a segment of pre-polymer (A) and/or as an additional pre-polymer, wherein said poly(ethylene glycol)
    i) has a molecular weight of from 200 to 1500 g/mol, preferably from 600 to 1000 g/mol; and/or
    ii) is present in an amount of from 5 wt. % to 20 wt. %, preferably of from 5 wt. % to 10 wt. %.

13. Composition according to claim 8, wherein said biologically active compound is a biologically active polypeptide having a molecular weight which is 10000 Da or less, preferably said multi-block copolymer contains poly(ethylene glycol), as a segment of pre-polymer (A) and/or as an additional pre-polymer, and wherein said poly(ethylene glycol)
    i) has a molecular weight of from 400 to 3000 g/mol, preferably from 600 to 1500 g/mol; and/or
    ii) is present in an amount of from 5 wt. % to 60 wt. %, preferably of from 5 wt. % to 40 wt. %.

14. Composition according claim 8, wherein said biologically active compound is a biologically active polypeptide having a molecular weight of 10 000 Da or more, preferably said multi-block copolymer contains poly(ethylene glycol), as a segment of pre-polymer (A) and/or as an additional pre-polymer, and wherein said poly(ethylene glycol)
    i) has a molecular weight of from 600 to 5000 g/mol, preferably of from 1000 to 3000 g/mol; and/or
    ii) is present in an amount of from 5 wt. % to 70 wt. %, more preferably of from 10 wt. % to 50 wt. %.

15. Composition according to claim 8, in the form of microspheres, microparticles, nanoparticles, nanospheres, rods, implants, gels, coatings, films, sheets, sprays, tubes, membranes, meshes, fibres, or plugs.

16. Composition according to claim 8, wherein the average diameter of the microspheres and/or microparticles is preferably in the range of 0.1-1000 μm, more preferably in the range of 1-100 even more preferably in the range of 10-50 μm.

17. Composition according to claim 16, wherein the biologically active compound is dissolved or dispersed throughout the polymer matrix.

18. Composition according to claim 16, wherein the microsphere comprises a reservoir wherein biologically active compound is contained, surrounded by a polymer in mononuclear or polynuclear state.

19. Composition according to claim 8 for treating rheumatoid arthritis, hepatitis, diabetes, metabolic syndromes, osteoarthritis, renal disease, inflammation, local pain processes, local infections, local skin diseases, tumours (or their sites after surgical removal as a postoperative treatment to destroy any tumour cells possibly remaining), prostate or breast cancer, agromegaly, ocular diseases, local brain diseases, and cardiovascular diseases.

20. A method for delivering a biologically active compound to a subject in need thereof, comprising administering an effective dose of a composition according to claim 8.

21. A method of manufacturing a composition according to claim 16, comprising the successive steps of
   a) emulsifying an aqueous solution of a water-soluble biologically active compound in a solution of a biodegradable, semi-crystalline, phase separated, thermoplastic multi-block copolymer comprising at least one hydrolysable pre-polymer (A) segment and at least one hydrolysable pre-polymer (B) segment; said multi-block copolymer having a Tg of 37° C. or less and a Tm of 110-250° C. under physiological conditions; the segments are linked by a multifunctional chain-extender; the segments are randomly distributed over the polymer chain; and at least part of the pre-polymer (A) segment is derived from a water-soluble polymer, in an organic solvent;
   b) subsequently emulsifying the resultant emulsion of a) in an aqueous solution comprising a surfactant, thereby yielding a water-in-oil-in-water (W/O/W) emulsion; and
   c) extracting the organic solvent to solidify microspheres.

22. A method of manufacturing a composition according to claim 16, comprising the successive steps of
   a) dispersing the biologically active compound as a solid powder in a solution of a biodegradable, semi-crystalline, phase separated, thermoplastic multi-block copolymer comprising at least one hydrolysable pre-polymer (A) segment and at least one hydrolysable prepolymer (B) segment: said multi-block copolymer having a Tg of 37° C. or less and a Tm of 110-250° C. under physiological conditions; the segments are linked by a multifunctional chain-extender; the segments are randomly distributed over the polymer chain; and at least part of the pre-polymer (A) segment is derived from a water-soluble polymer, in an organic solvent;
   b) emulsifying the resultant dispersion of a) in an aqueous solution comprising a surfactant, thereby yielding a solid-in-oil-in-water (S/O/W) emulsion; and
   c) extracting the organic solvent to solidify the microspheres.

23. A method of manufacturing a composition according to claim 1, comprising the successive steps of
   a) emulsifying an aqueous solution of a water-soluble biologically active compound in a solution of a biodegradable, semi-crystalline, phase separated, thermoplastic multi-block copolymer comprising at least one hydrolysable pre-polymer (A) segment and at least one hydrolysable pre-polymer (B) segment; said multi-block copolymer having a Tg of 37° C. or less and a Tm of 110-250° C. under physiological conditions; the segments are linked by a multifunctional chain-extender; the segments are randomly distributed over the polymer chain; and at least part of the pre-polymer (A) segment is derived from a water-soluble polymer, in an organic solvent;
   b) adding a polymer precipitant, to the resultant emulsion of a) to form embryonic microparticles; and
   c) extracting the polymer precipitant and the organic solvent to solidify the microspheres.

24. A method of manufacturing a composition according to claim 16, comprising the successive steps of
   a) dispersing the biologically active compound as a solid powder in a solution of a biodegradable, semi-crystalline, phase separated, thermoplastic multi-block copolymer comprising at least one hydrolysable pre-polymer (A) segment and at least one hydrolysable prepolymer (B) segment: said multi-block copolymer having a Tg of 37° C. or less and a Tm of 110-250° C. under physiological conditions; the segments are linked by a multifunctional chain-extender; the segments are randomly distributed over the polymer chain; and at least part of the pre-polymer (A) segment is derived from a water-soluble polymer, in an organic solvent;
   b) adding a polymer precipitant, to the resultant dispersion of a) to form embryonic microparticles; and
   c) extracting the polymer precipitant and the organic solvent to solidify the microspheres.

25. Biodegradable, semi-crystalline, phase separated, thermoplastic multi-block copolymer according to claim 1, wherein said aliphatic chain-extender is 1,4-butane diisocyanate.

26. Biodegradable, semi-crystalline, phase separated, thermoplastic multi-block copolymer according to claim 3, wherein said non cyclic monomers are selected from the group consisting of succinic acid, glutaric acid, adipic acid, sebacic acid, lactic acid, glycolic acid, hydroxybutyric acid, ethylene glycol, diethylene glycol, 1,4-butanediol and/or 1,6-hexanediol, and wherein said cyclic monomers are selected from the group consisting of glycolide, lactide, ε-caprolactone, δ-valerolactone, trim ethylene carbonate, tetramethylenecarbonate, 1,5-dioxepane-2-one, 1,4-dioxane-2-one (para-dioxanone) and/or cyclic anhydrides.

27. Biodegradable, semi-crystalline, phase separated, thermoplastic multi-block copolymer according to claim 1, wherein said water-soluble polymer is derived from poly (ethylene glycol) (PEG) having a Mn of 150-5000 g/mol.

28. Biodegradable, semi-crystalline, phase separated, thermoplastic multi-block copolymer according to claim 5, wherein said pre-polymer (B) segment comprises l-lactide pre-polymers and d-lactide pre-polymers in such amounts and ratio that stereocomplexation between l-lactide and d-lactide is achieved.

29. Biodegradable, semi-crystalline, phase separated, thermoplastic multi-block copolymer according to claim 28, wherein said pre-polymer (B) segment is poly(l-lactic acid) with an Mn of 1000 g/mol or more.

30. Biodegradable, semi-crystalline, phase separated, thermoplastic multi-block copolymer according to claim 29, wherein said pre-polymer (B) segment is poly(l-lactic acid) with an Mn of 2000 g/mol or more.

31. Biodegradable, semi-crystalline, phase separated, thermoplastic multi-block copolymer according to claim 29, wherein said pre-polymer (B) segment is poly(l-lactic acid) with an Mn of 3000 g/mol or more.

32. Biodegradable, semi-crystalline, phase separated, thermoplastic multi-block copolymer according to claim 6, wherein said swelling ratio under physiological conditions varies from 1 to 2.

33. Biodegradable, semi-crystalline, phase separated, thermoplastic multi-block copolymer according to claim 32, wherein said swelling ratio under physiological conditions varies from 1 to 1.5.

34. Biodegradable, semi-crystalline, phase separated, thermoplastic multi-block copolymer according to claim 7, wherein said copolymer has an intrinsic viscosity of between 0.2 and 2 dl/g.

* * * * *